US012661373B2

(12) United States Patent
Baronian et al.

(10) Patent No.: US 12,661,373 B2
(45) Date of Patent: Jun. 23, 2026

(54) ELECTROCHEMICALLY ACTIVATED SALT SOLUTION

(71) Applicant: AZAD Pharma AG, Schaffhausen (CH)

(72) Inventors: Mihran Baronian, Toffen (CH); Fabio Carli, Trieste (IT); Elisabetta Chiellini, Trieste (IT); Ernest Baehler, Egg (CH)

(73) Assignee: AZAD PHARMA AG, Schaffhausen (CH)

( * ) Notice: Subject to any disclaimer, the term of this patent is extended or adjusted under 35 U.S.C. 154(b) by 833 days.

(21) Appl. No.: 17/259,458

(22) PCT Filed: Jul. 10, 2019

(86) PCT No.: PCT/EP2019/068574
§ 371 (c)(1),
(2) Date: Jan. 11, 2021

(87) PCT Pub. No.: WO2020/011870
PCT Pub. Date: Jan. 16, 2020

(65) Prior Publication Data
US 2021/0275579 A1 Sep. 9, 2021

(30) Foreign Application Priority Data

Jul. 12, 2018 (EP) ..................................... 18183127

(51) Int. Cl.
| | |
|---|---|
| *A61K 33/22* | (2006.01) |
| *A61K 9/00* | (2006.01) |
| *A61K 9/08* | (2006.01) |
| *A61K 33/20* | (2006.01) |
| *A61K 33/42* | (2006.01) |
| *A61P 27/02* | (2006.01) |
| *A61P 31/04* | (2006.01) |
| *A61P 31/12* | (2006.01) |
| *C25B 1/26* | (2006.01) |
| *C25B 11/02* | (2021.01) |

(52) U.S. Cl.
CPC ........... *A61K 33/22* (2013.01); *A61K 9/0048* (2013.01); *A61K 9/08* (2013.01); *A61K 33/20* (2013.01); *A61K 33/42* (2013.01); *A61P 27/02* (2018.01); *A61P 31/04* (2018.01); *A61P 31/12* (2018.01); *C25B 1/26* (2013.01); *C25B 11/02* (2013.01)

(58) Field of Classification Search
None
See application file for complete search history.

(56) References Cited

U.S. PATENT DOCUMENTS

| | | |
|---|---|---|
| 7,393,522 B2 | 7/2008 | Najafi et al. |
| 8,691,289 B2 | 4/2014 | Chen et al. |
| 2004/0137078 A1 | 7/2004 | Najafi et al. |
| 2009/0092685 A1 | 4/2009 | Selkon |
| 2010/0266710 A1 | 10/2010 | Baronian |
| 2010/0330204 A1 | 12/2010 | Chen et al. |
| 2012/0237616 A1* | 9/2012 | Panicheva ............... A61P 37/08 |
| | | 424/661 |

FOREIGN PATENT DOCUMENTS

| | | |
|---|---|---|
| CN | 1678328 A | 10/2005 |
| CN | 101163491 A | 4/2008 |
| CN | 105213299 A | 1/2016 |
| EP | 2431056 A1 | 3/2012 |
| JP | H 10-236961 A | 9/1998 |
| WO | 03/042111 A2 | 5/2003 |
| WO | 03050044 A1 | 6/2003 |
| WO | 2004/031077 A2 | 4/2004 |
| WO | 2005/065388 A2 | 7/2005 |
| WO | WO-2008089268 A2 * | 7/2008 ............. A61K 33/20 |
| WO | 2009/013019 A2 | 1/2009 |
| WO | 2012034659 A2 | 3/2012 |
| WO | 2013/050562 A1 | 4/2013 |
| WO | 2015/001423 A2 | 1/2015 |
| WO | 2016/100543 A2 | 6/2016 |

OTHER PUBLICATIONS

Thorn et al., "Electrochemically activated solutions: evidence for antimicrobial efficacy and applications in healthcare enviroments", Eur J Clin Microbiol Infect Dis, Aug. 2, 2011, vol. 31, No. 5, 641-653 pages.
European Medicines Agency et al., "Background review for the excipient boric acid", revision of the guideline on Excipients in the label and package leaflet of medicinal products for human use (CPMP/463/00 Rev. 1), Jul. 23, 2015 pp. 1-19.
Gerald E Lowther: "Chapter 13—Preparation used with contact lenses" in: "Clinical Ocular Pharmacology", Jan. 1, 1989, p. 338.
International Search Report and Written Opinion cited in PCT/EP2019/068574, dated Sep. 10, 2019, 15 pages.
Extended European Search Report cited in EP 18183127.2 dated Jan. 22, 2019, 12 pages.
O'Brien et al.: "Topical Ciprofloxacin Treatment of Pseudomonas Keratitis in Rabbits", Arch Ophthalmol., vol. 106, No. 10, 1988, pp. 1444-1446.
Huang et al.: "Application of electrolyzed water in the food industry", Food Central, vol. 19, 2008, pp. 329-345.
Romanowski et al.: "The successful treatment of gatifloxacin-resistant *Staphylococcus aureus* keratitis with Zymar (gatifloxacin 0.3%) in a NZW rabbit model", Am J Ophthalmol., vol. 139, No. 5, 2005, pp. 867-877.
Willcox: "Review of resistance of ocular isolates of Pseudomonas aeruginosa and staphylococci from keratitis to ciprofloxacin, gentamicin and cephalosporins", Clin Exp Optom, vol. 94, No. 2, 2011, pp. 161-168.

(Continued)

*Primary Examiner* — H. Sarah Park

(74) *Attorney, Agent, or Firm* — Rothwell, Figg, Ernst & Manbeck, P.C.

(57) ABSTRACT

The present application refers to an electrochemically activated salt solution (ECAS), its production, and its use for treating infections.

12 Claims, 4 Drawing Sheets

(56)               References Cited

OTHER PUBLICATIONS

Figure 1:
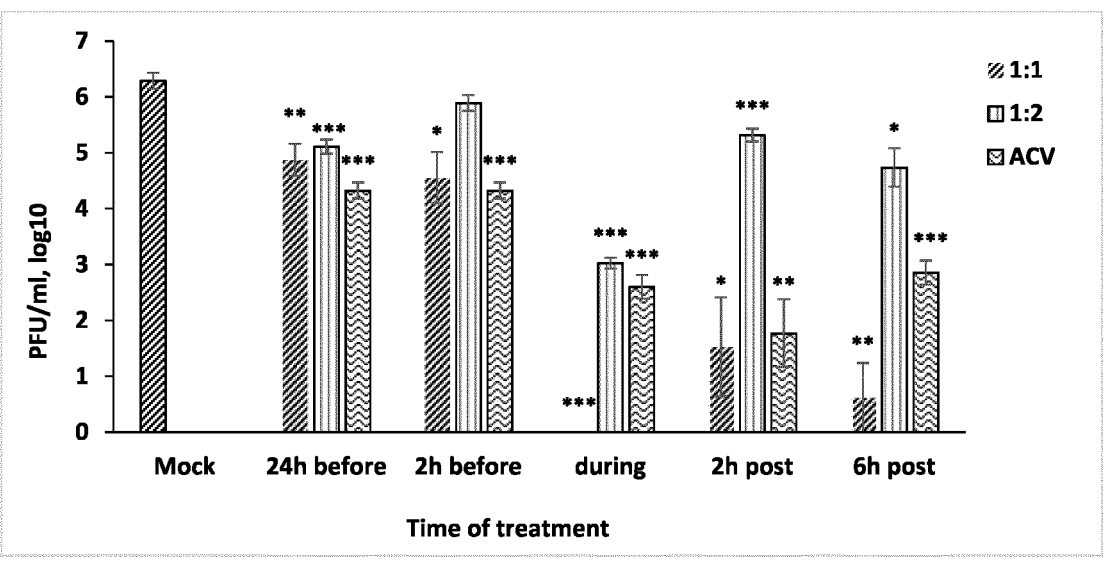

O'Callaghan: "Chapter 42—The Rabbit Intrastromal Injection Model of Bacterial Keratitis", Handbook of Animal Models of Infection, Experimental Models in Antimicrobial Chemotherapy, 1999, pp. 367-374.

O'Brien: "Management of bacterial keratitis: beyond exorcism towards consideration of organism and host factors", Eye, vol. 17, 2003, pp. 957-974.

* cited by examiner

ELECTROCHEMICALLY ACTIVATED SALT SOLUTION

CROSS REFERENCE TO RELATED APPLICATION

This application is a 35 U.S.C. 371 National Phase Entry Application from PCT/EP2019/068574, filed Jul. 10, 2019, which claims the benefit of European Patent Application No. 18183127.2 filed on Jul. 12, 2018, the disclosures of which are incorporated herein in their entirety by reference.

The present application refers to an electrochemically activated salt solution (ECAS), its production, and its use for treating infections.

Electrochemically activated salt solutions are usually obtained by electrolysis of sodium chloride solutions. Electrochemically activated salt solutions are known as cleaning or disinfection agents e.g. in agriculture, dentistry, medicine and food industry. It can be used in applications like surface disinfection, e.g. of working plates, tables, floors, etc., for cold sterilizing procedures in agriculture, for the elimination of microbial organisms, for wash and laundry application, in swimming pools and even as prophylaxis against athletes foot.

WO 2004/031077 discloses a device for producing a biocidal solution by electrolytic treatment of an aqueous salt solution. WO 2005/065388 discloses an oxidative reduction potential water solution and its use as disinfectant of a wound treatment.

JP 1997/0040444 discloses an acidic ECAS having a pH from 2.0 to 6.0 for use as an ophthalmic preparation.

US 2010/0330204 discloses an acidic ECAS having a pH from 1.0 to 4.0 for the treatment of an outer eye disorder selected from cataract, ocular keratitis, corneal neovascularization, epithelium deficiency, and chronic opacity.

WO 2009/013019 discloses two-phase pharmaceutical preparations comprising an active ingredient and an ECAS for medical applications. ECAS is also suggested as a carrier for the manufacture of pharmaceutical preparations.

Ocular infections may cause serious ocular problems with significant sight-threatening consequences if-mostly aggressive-therapy is not promptly instituted. For several years, cephalosporins and aminoglycosides have been used as first choice treatment for infectious eye diseases. However, problems associated with topical antibiotics and the emergence of antibiotic-resistant organisms have prompted interest in the search for therapeutic alternatives (Romanowski et al., 2005, Willcox, 2011).

Also the use of preservatives, such as benzalkoniumchloride (BAK), in ophtalmics is recently debated due to allergic reactions. On the other hand, preservative-free medicaments are usually offered only in single-use units. Moreover, preservative-free formulations typically have an acidic pH value of less than 5, while the recommended pH value of ophthalmica is neutral to slightly alkaline to avoid irritations of the eye and to enable high patients' compliance.

Considering the above, there is an urgent need of new preparations for the treatment of eye infections which overcome the drawbacks of the known medicaments.

Thus, the object of the present invention is the provision of an effective medicament which is stable over a prolonged period of time and improves the patients' compliance by minimizing any harmful side effects, when applying the same.

In a first aspect, the present invention refers to an electrochemically activated salt solution (ECAS) comprising a content of total chlorine of between 1 and 500 mg/l, preferably of between 100-450 mg/l, a content of chloride of between 2 and 8 g/l, preferably of between 3 and 7 g/l, a redox potential of +150 to +1,350 mV, preferably of +600 to +1,100 mV, more preferably of +700 to +1,050 mV, more preferably +700 to +1,000 mV, an osmolality of 20-800, preferably 200-400 mOsm/kg, more preferably of 250-350 mOsm/kg, and a pH value of 6.0-7.8, preferably of 6.2-7.6, more preferably of 7.1-7.4.

The ECAS of the invention may further comprise at least one (salt of) boric acid and/or at least one (salt of) phosphoric acid. The ECAS of the invention preferably further comprises at least one salt of boric acid and/or at least one salt of phosphoric acid, more preferably at least one salt of phosphoric acid. In another embodiment the ECAS of the invention further comprises at least one salt of boric acid. In another embodiment, the ECAS of the invention further comprises at least one salt of boric acid and at least one salt of phosphoric acid.

Salts of boric acid are usually borates ($BO_3^{3-}$). Salts of phosphoric acid may include phosphate ($PO_4^{3-}$), hydrogenphosphate ($HPO_4^{2-}$) and/or dihydrogen phosphate ($H_2PO_4^-$). Suitable counterions of the above salts are alkali ions, such as sodium ($Na^+$) and potassium ($K^+$), ammonium ($NH_4^+$), or $Ca^{2+}$. In a preferred embodiment the ECAS of the invention comprises sodium dihydrogenphosphate further and disodium hydrogenphosphate.

The (salt of) phosphoric acid—if present—is preferably present in a total amount of 0.01-1000 g/l, more preferably in a total amount of 0.1-100 g/l. The (salt of) boric acid—if present—is preferably present in a total amount of 0.01 to 1000 g/l, more preferably in a total amount of 0.1-500 g/l.

The electrochemically activated salt solution is preferably stable over one year, more preferably over two years, when stored in a closed high-density polyethylene (HDPE) container at 20° C. It was surprisingly found that ECASs comprising at least one (salt of) boric acid and/or at least one (salt of) phosphoric acid may even improve the stability of the ECAS of the invention as compared to ECASs of the invention lacking at least one (salt of) boric acid and/or at least one (salt of) phosphoric acid. Moreover, it has been found that storage in high-density polyethylene material (HDPE) provided good stability as compared to other materials, such as low density polyethylene (LDPE) or polypropylene (PP).

In one embodiment, "stable" or "stability" in the sense of the present invention means that the redox potential of the ECAS of the present invention is reduced by 20%, preferably 1-10% at maximum after 6 months of storage under the respective storing conditions. Alternatively, the redox potential of the ECAS of the present invention is reduced by 25%, preferably 1-10%, at maximum after 12 months of storage under the respective storing conditions. Alternatively, the redox potential of the ECAS of the present invention is reduced by 30%, preferably 2-15%, at maximum after 24 months of storage under the respective storing conditions.

The redox potential can be determined via established methods known to the skilled person.

In a further aspect, the ECAS according to the present invention may contain hypochlorite ions and/or hypochlorous acid, particularly in a total concentration of 1 to 10000 mg/l, more preferably in a total concentration of 10 to 1000 mg/l.

The total content of chlorite and/or chlorate ions is preferably below toxic levels, e.g. less than 10 mg/l, more preferably 0.001-10 mg/l, even more preferably 0.001-4 mg/l.

Further, the total content of heavy metals and heavy metal ions in the ECAS according to the invention is preferably below toxic levels, e.g. less than 10 μg/g, preferably less than 6 μg/g, more preferably between 0.001 and 6 μg/g, and the content of each individual heavy metal and heavy metal ion is preferably less than 0.5 μg/g. Heavy metals and heavy metal ions may be or derive from silver, arsenic, gold, iridium, palladium, platinum, rhodium, thallium, cadmium, cobalt, mercury, lead, ruthenium, chromium, molybdenum, antimony, tin copper, nickel, osmium, or vanadium. The heavy metal (ion) may be detected by ICP-MS analysis according to ISO 17025.

In a further aspect, the ECAS of the invention may contain at least one viscosity-increasing agent, such as a polymer. Any polymer may be used either organic or inorganic. Suitable polymers may be cellulose, cellulose derivatives, such as carboxymethyl (CMC), or hydroxypropyl methylcellulose (HPMC), polysaccharides, such as glucosaminoglycans, e.g. hyaluronic acid (HA), polyvinyl alcohol (PVA), polyvinyl pyrrolidone (PVP), silica gel, magnesium metasilicate and/or aluminum-metasilicate.

The ECAS of the invention preferably does not contain, i.e. is free of, an additional therapeutically active agent, such as a drug. It has surprisingly been found that the ECAS of the invention is effective in the treatment of eye infections without the need of additional therapeutically active agents.

The ECAS of the invention preferably does not contain, i.e. is free of, an additional preservative, such as BAK, sodium perborate, oxychloro complex, zinc borate complex, etc. It has surprisingly been found that the ECAS of the invention has sufficient disinfecting power per se to prevent microbial growth.

In a further aspect, the present invention relates to a process for producing an electrochemically activated salt solution (ECAS) as described above comprising the steps of (i) electrolyzing an aqueous chloride solution in an electrolysis reactor, (ii) optionally adding at least one (salt of) boric acid and/or at least one (salt of) phosphoric acid, and (iii) optionally diluting the ECAS, preferably by adding water for injection.

The electrolysis reactor preferably includes a cylindrical cathode, which is mounted coaxially within a cylindrical anode. The cathode and the anode may be separated by a microporous membrane, wherein an electrical current is applied to the electrodes. The electrolysis is conducted at a current of 10.0-30.0 A, preferably at a current of 15.0-20.0 A.

The electrolysis reactor is preferably configured for continuous electrolysis. One or more of said reactors can be combined in parallel or serially.

The aqueous chloride solution used in step (i) preferably has a concentration of up to 10 g/l, preferably 2-9 g/l, in water for injection (sterile water).

The ECAS obtained in step (i) or (ii) may be diluted with an aqueous medium, preferably sterile water. The ECAS obtained in step (i) or (ii) may e.g. be diluted with an aqueous medium in a ratio of ECAS:aqueous medium of from 1:6 to 6:1, preferably 1:0.5 to 1:3.

In a further aspect, the present invention relates to a pharmaceutical preparation comprising an electrochemically activated salt solution (ECAS) of the invention and optionally at least one therapeutically effective agent. The pharmaceutical preparation according to the invention may comprise at least one pharmaceutically acceptable excipient. Pharmaceutically acceptable excipients may be selected from e.g. buffers, adjuvants, auxiliary agents, fillers, diluents, etc.

In another aspect, the electrochemically activated salt solution (ECAS) of the invention is for use in treating infections, particularly eye infections, e.g. caused by microbes such as bacteria, fungi and/or viruses. Bacterial and fungal infections might be caused by one or more species selected from the group consisting of *Staphylococcus aureus*, methicillin-resistant *Staphylococcus aureus* (MRSA), *Escherichia coli*, *Staphylococcus epidermidis*, *Pseudomonas aeruginosa*, *Acinetobacter calcoaceticus*, *Enterobacter aerogenes*, *Streptococcus anginosus*, *Streptococcus pyogenes*, *Candida albicans*, *Aspergillus brasiliensis*, *Aerratia marcescens* and *Acinetobacter pitii*. Viral infections might be caused by viruses selected from the group consisting of adenoviruses, such as human adenovirus B and human adenovirus C, enteroviruses, such as enterovirus 70 or coxsackie viruses, and herpesviruses, such as Herpes simplex virus 1 and Herpes simplex virus 2.

In a further aspect, the electrochemically activated salt solution (ECAS) of the invention can be particularly used for treating eye infections preferably for treating conjunctivitis, keratitis, blepharitis, endophthalmitis, more preferably keratitis and/or conjunctivitis, even more preferably conjunctivitis. It was surprisingly found that the ECAS of the invention revealed optimum efficacy in the treatment of bacterial conjunctivitis and bacterial keratitis by in vitro and in vivo studies without causing detrimental side-effects.

Thus, in a very preferred embodiment, the electrochemically activated salt solution (ECAS) of the invention can be used for treating conjunctivitis, e.g. caused by microbes, e.g. bacteria, fungi or viruses, more preferably for treating bacterial conjunctivitis.

Thus, in another preferred embodiment, the electrochemically activated salt solution (ECAS) of the invention can be used for treating keratitis, e.g. bacterial keratitis.

For treating eye infections the electrochemically activated salt solution (ECAS) of the invention may be administered topically onto the eye, the lacrimal sac and/or the lid. In a preferred embodiment, the ECAS of the invention may be administered onto the eye directly after infection.

FIGURES

FIG. 1 Titer of the HSV-1 strain Kupka. Vero cells were treated with the test products (24 h and 2 h before infection, during infection, 2 and 6 h post infection), and infected with HSV-1 strain Kupka at a multiplicity of infection (MOI) of 0.01. The infected cells were collected at 24 hours post infection (hpi) and the virus titer was determined by plaque assay. MOCK—infected untreated cells; 1:1—infected cells treated with the ECAS2 diluted 1:1, 100 μl; 1:2—infected cells treated with the ECAS2 diluted 1:2, 100 μl; ACV—infected cells treated with aciclovir, 100 μM.

Figure 2:
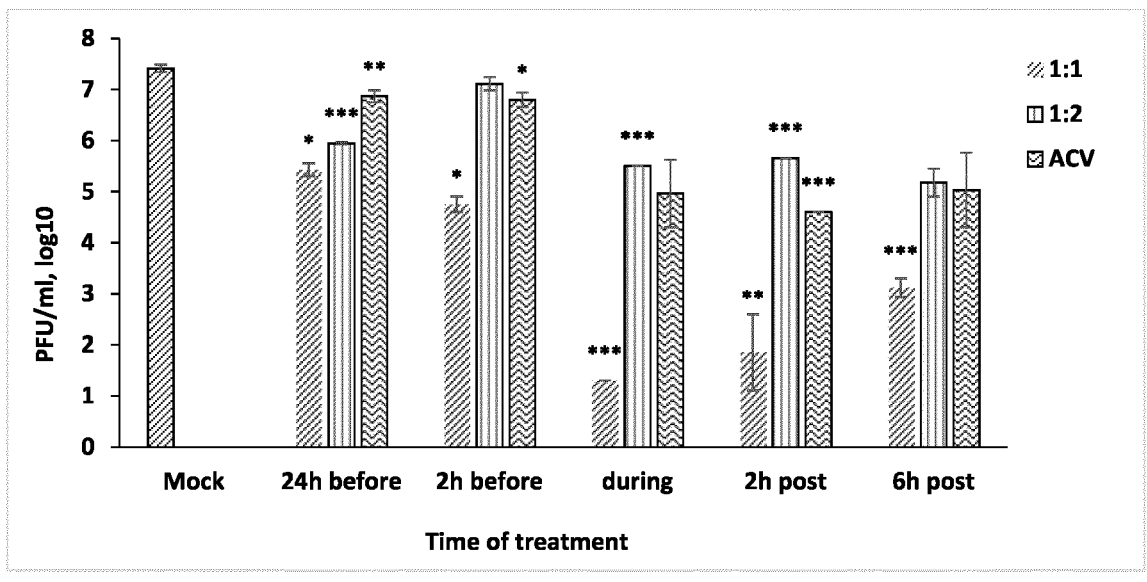

FIG. 2 Titer of the HSV-1 strain ANGpath. Vero cells were treated with the test products 24 h and 2 h before infection, during infection, 2 and 6 h post infection, and infected with HSV-1 strain ANGpath at a MOI of 0.01. The infected cells were collected 24 hpi and the virus titer was determined by plaque assay. MOCK-infected untreated cells; 1:1—infected cells treated with the ECAS2 diluted 1:1, 100 μl; 1:2—infected cells treated with the ECAS2 diluted 1:2, 100 μl; ACV—infected cells treated with aciclovir, 100 μM.

5

Figure 3:
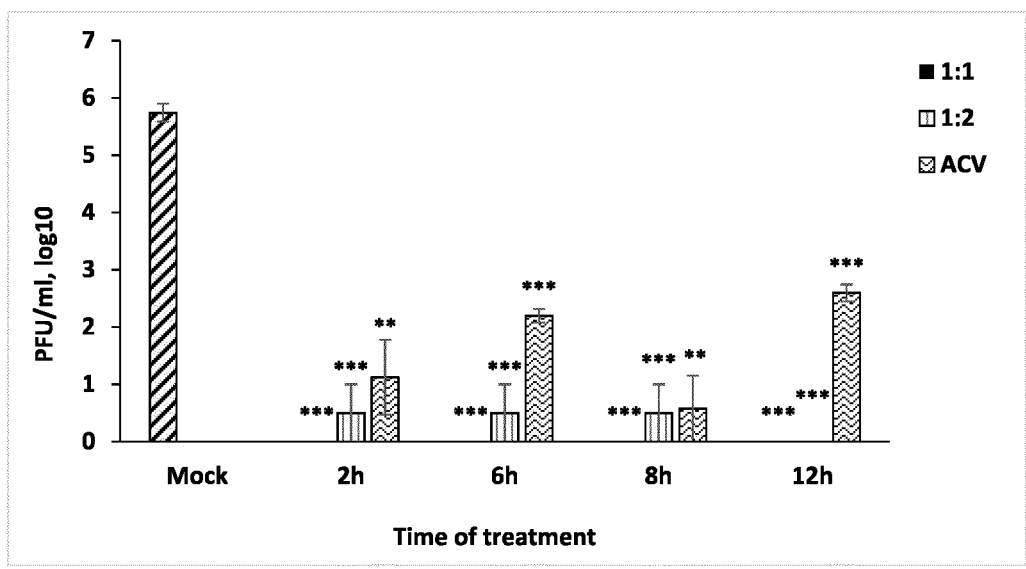

FIG. 3 Titer of the HSV-1 strain Kupka. HSV-1 strain Kupka (MOI 0.01) was incubated with the test products for 2, 6, 8 or 12 h before the infection of Vero cells. The infected cells were collected at 24 hpi and the virus titer was determined by plaque assay. MOCK-cells infected with untreated virus; 1:1—infected cells treated with the ECAS2 diluted 1:1, 100 μl; 1:2—infected cells treated with the ECAS2 diluted 1:2, 100 μl; ACV—infected cells treated with aciclovir, 100 μM.

Figure 4:
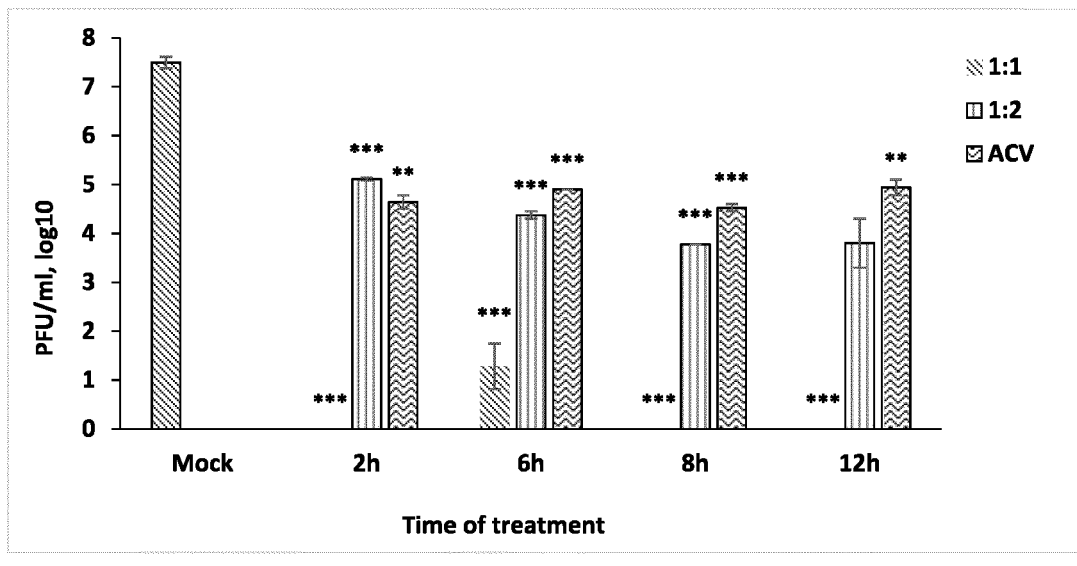

FIG. 4 Titer of the HSV-1 strain ANGpath. ANGpath (MOI 0.01) was incubated with the test products for 2, 6, 8 or 12 h before the infection of Vero cells. The infected cells were collected at 24 hpi and the virus titer was determined by plaque assay. MOCK—cells infected with untreated virus; 1:1—infected cells treated with ECAS2 diluted 1:1, 100 μl; 1:2—infected cells treated with the ECAS2 diluted 1:2, 100 μl; ACV—infected cells treated with aciclovir, 100 μM.

Figure 5:
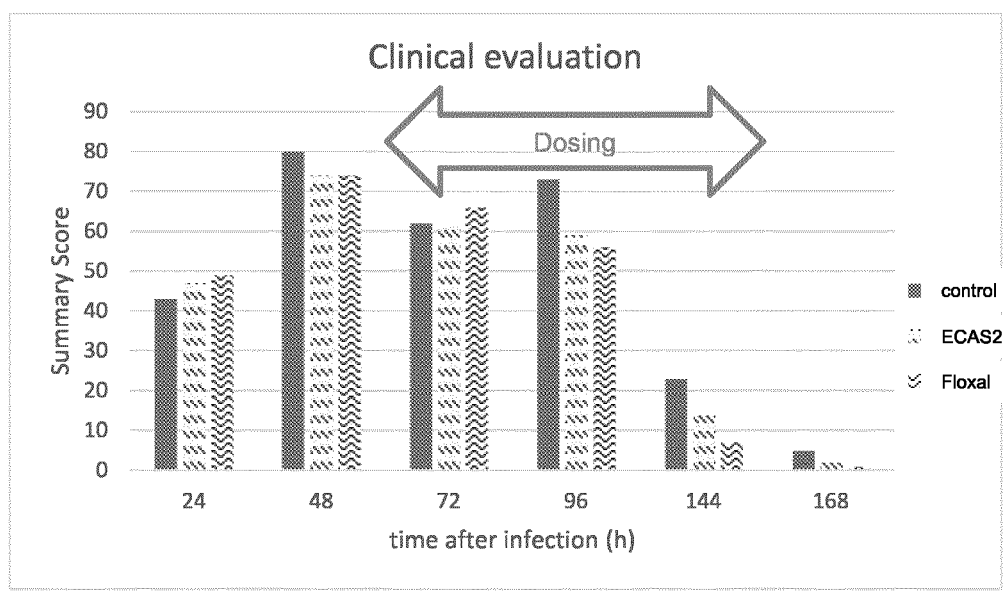

FIG. 5 Summary score of the ophthalmological evaluation of ECAS2 and Floxal® treated rabbit eyes infected with *Staphylococcus aureus*. Rabbit eyes were treated within 6 days. 24, 48, 72, 96, 144 and 168 hpi the ophthalmological evaluation was performed. The main parameters of conjunctivitis were graded 1, 2, 3 or 4 for each quadrant. The observations were summarized per group. The number of eyes per group n was 8.

Figure 6:
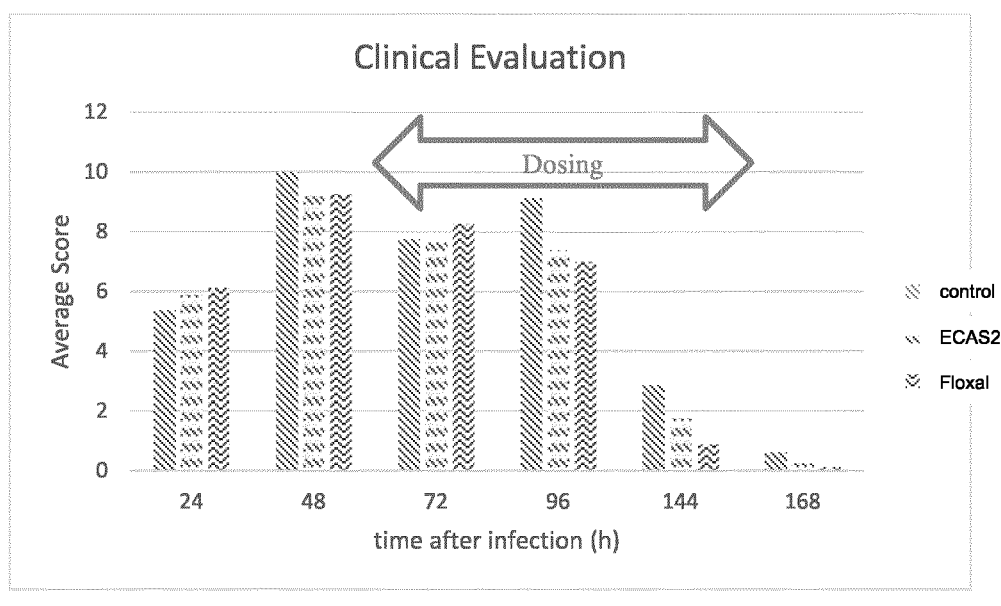

FIG. 6 Average score of the ophthalmological evaluation of ECAS2 and Floxal® treated rabbit eyes infected with *Staphylococcus aureus*. Rabbit eyes were treated for 6 days. 24, 48, 72, 96, 144 and 168 hpi the ophthalmological evaluation was performed. The main parameters of conjunctivitis were graded 1, 2, 3 or 4 for each quadrant. The observations were expressed as average score per group. The number of eyes per group n was 8.

Figure 7:
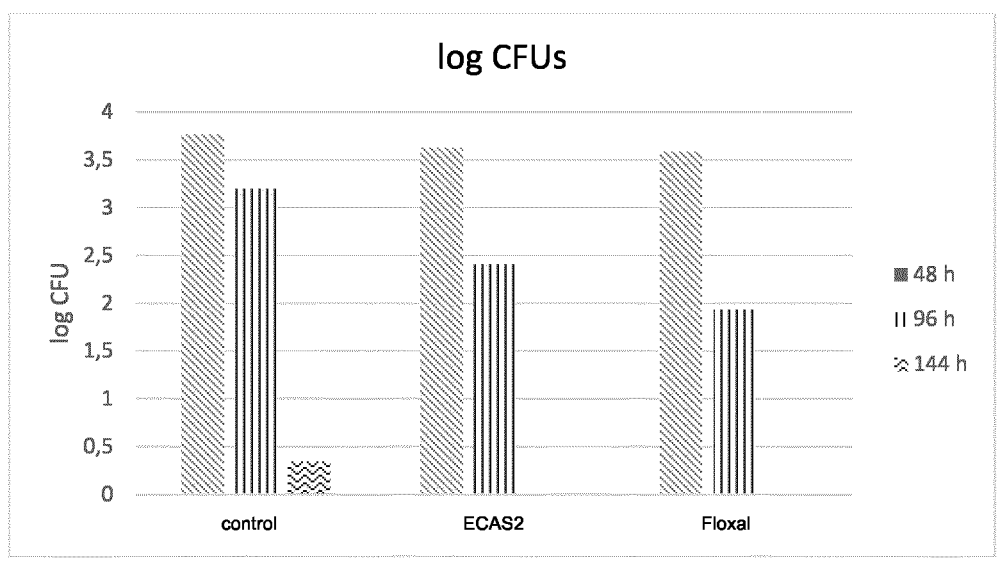

FIG. 7 Colony-forming units (CFUs) found in ECAS2 and Floxal® treated rabbit eye conjunctivas infected with *Staphylococcus aureus*. Rabbit eyes were treated for 6 days. 24, 48, 72, 96, and 144 hpi the ophthalmological evaluation was performed. The observations were summarized per group. The number of eyes per group n was 8.

Figure 8:
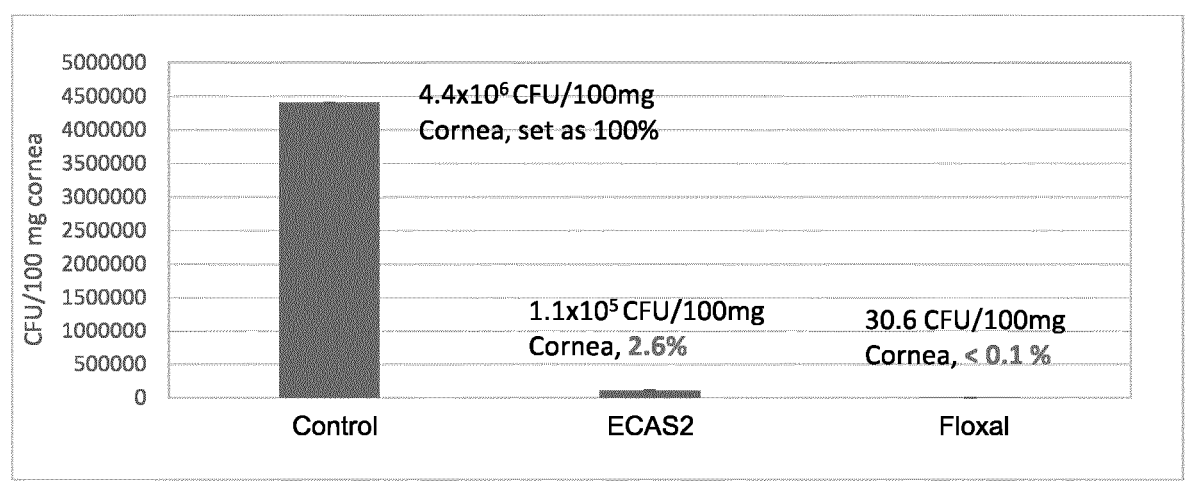

FIG. 8 ECAS2 and Floxal® (0.3% Ofloxacin) treated rabbit eyes infected with *Pseudomonas aeruginosa*. Rabbit eyes were treated every hour from 6 to 19 h post infection. Following sacrifice of the rabbits, the number of viable *Pseudomonas aeruginosa* per 100 mg of cornea was quantified. The number of eyes per group n was 5.

The present invention shall be further illustrated in more detail but not limited by the following examples.

EXAMPLE 1: Preparation and Characterization of Electrochemically Activated Salt Solutions For the preparation of ECAS six combined electrolysis reactors (coaxial electrodes) were used. Saturated sodium chloride solution stored in a tank was applied through a valve at a predetermined ratio to a flow of pure water for injection e.g. with a flow rate of 2.83 l/min and then pumped through the reactors. The two activated solutions generated by the anode and the cathode were collected and mixed at a predetermined ratio to give pure ECAS.

Optionally, borate and/or phosphate salts were added to the pure ECAS before dilution with water for injection.

The ECAS obtained are summarized in the following table.

TABLE 1

| Composition of ECAS | | | |
| --- | --- | --- | --- |
| | ECAS 0 | ECAS 1 (including boric acid) | ECAS 2 (including phosphates) |
| ECAS obtained from step (i) [wt.-%] | 50 | 49.83 | 48.58 |
| Boric acid (H$_3$BO$_3$) [wt.-%] | | 0.15 | |
| NaH$_2$PO$_4$ [wt.-%] | | | 0.27 |
| Na$_2$HPO$_4$ [wt.-%] | | | 1.15 |
| water for injection [wt.-%] | 50 | 49.83 | 50.00 |
| NaOH (1M) [wt.-%] | | 0.19 | |
| pH | 7.5 | 7.3 | 7.4 |
| redox potential (mV) | 907 | 871 | 856 |
| total chlorine (ppm) | 313 | 290 | 302 |
| osmolarity (mOsm/kg) | 305 | 326 | 315 |

EXAMPLE 2: Stability of Electrochemically Activated Salt Solutions

The stability of electrochemically activated salt solutions was evaluated by storing the obtained ECAS (see Table 1) in a closed, high-density polyethylene (HDPE) container at 20° C.

TABLE 2a

| Stability of ECAS 0, ECAS 1 and ECAS 2 over a period of 6 and 12 month | | | | |
| --- | --- | --- | --- | --- |
| Storage | | ECAS 0 | ECAS 1 | ECAS 2 |
| 0 month | pH | 7.5 | 7.3 | 7.4 |
| | redox (mV) | 907 | 871 | 856 |
| | total chlorine (ppm) | 313 | 290 | 302 |
| | Time Kill Anti-Bacterial Test [1] | positive | positive | positive |
| 6 month | pH | 5.5 | 7.3 | 7.40 |
| | redox (mV) | 1010 | 886 | 841 |
| | total chlorine (ppm) | 128 | 230 | 190 |
| | Time Kill Anti-Bacterial Test 1 | positive | positive | positive |
| 12 month | pH | 5.7 | 7.2 | 7.4 |
| | redox (mV) | 961 | 873 | 833 |
| | total chlorine (ppm) | 94 | 160 | 142 |
| | Time Kill Anti-Bacterial Test 1 | reduced | positive | positive |

[1] The Time Kill Antibacterial Test is an in-vitro test measuring the number of bacteria killed at different times after inoculation of ECAS in the bacterial suspension. The detailed results of this test on all ECAS samples at different storage times are reported in Table 2b, 2c, 2d TABLE 2b

| Antibacterial activity (Time Kill Anti-bacterial test) of ECAS 0 over storage | | | | | |
| --- | --- | --- | --- | --- | --- |
| ECAS SAMPLE | STORAGE TIME | BACTERIA Conc. CFU/ml | EXPOSURE TIME | BACTERIA SURVIVED CFU/ml | PERCENT REDUCTION |
| ECAS 0 | 0 | *Staphylococc. aureus* 1.5 × 10$^6$ | 1 min | <10 | 99.9999% |
| | | | 5 min | <10 | 99.9999% |
| | | | 15 min | <10 | 99.9999% |

TABLE 2b-continued

Antibacterial activity (Time Kill Anti-bacterial test) of ECAS 0 over storage

| ECAS SAMPLE | STORAGE TIME | BACTERIA Conc. CFU/ml | EXPOSURE TIME | BACTERIA SURVIVED CFU/ml | PERCENT REDUCTION |
|---|---|---|---|---|---|
| | | | 30 min | <10 | 99.9999% |
| | | | 60 min | <10 | 99.9999% |
| | | Pseudomonas | 1 min | <10 | 99.9999% |
| | | aeruginosa | 5 min | <10 | 99.9999% |
| | | $1.6 \times 10^6$ | 15 min | <10 | 99.9999% |
| | | | 30 min | <10 | 99.9999% |
| | | | 60 min | <10 | 99.9999% |
| | 6 months | Staphylococc. | 1 min | <10 | 99.9999% |
| | | aureus | 5 min | <10 | 99.9999% |
| | | $6.4 \times 10^6$ | 15 min | <10 | 99.9999% |
| | | | 30 min | <10 | 99.9999% |
| | | | 60 min | <10 | 99.9999% |
| | | Pseudomonas | 1 min | <10 | 99.9999% |
| | | aeruginosa | 5 min | <10 | 99.9999% |
| | | $4.9 \times 10^6$ | 15 min | <10 | 99.9999% |
| | | | 30 min | <10 | 99.9999% |
| | | | 60 min | <10 | 99.9999% |
| | 12 months | Staphylococc. | 1 min | $6.1 \times 10^5$ | 89.8300% |
| | | Aureus | 5 min | $5.2 \times 10^5$ | 91.3300% |
| | | $6.0 \times 10^6$ | 15 min | $5.3 \times 10^5$ | 91.1700% |
| | | | 30 min | $5.5 \times 10^5$ | 90.8300% |
| | | | 60 min | $5.2 \times 10^5$ | 91.3300% |
| | | Pseudomonas | 1 min | $4.1 \times 10^5$ | 87.9400% |
| | | Aeruginosa | 5 min | $4.2 \times 10^5$ | 87.6500% |
| | | $3.4 \times 10^6$ | 15 min | $4.1 \times 10^5$ | 87.9400% |
| | | | 30 min | $3.2 \times 10^5$ | 90.5900% |
| | | | 60 min | $3.4 \times 10^5$ | 90.0000% |

TABLE 2c

Antibacterial activity (Time Kill Anti-bacterial test) of ECAS 1 over storage

| ECAS SAMPLE | STORAGE TIME | BACTERIA Conc. CFU/ml | EXPOSURE TIME | BACTERIA SURVIVED CFU/ml | PERCENTAGE REDUCTION |
|---|---|---|---|---|---|
| ECAS 1 | 0 | Staphylococcus | 1 min | <10 | 99.9999% |
| | | aureus | 5 min | <10 | 99.9999% |
| | | $4.8 \times 10^6$ | 15 min | <10 | 99.9999% |
| | | | 30 min | <10 | 99.9999% |
| | | | 60 min | <10 | 99.9999% |
| | | Pseudomonas | 1 min | <10 | 99.9999% |
| | | aeruginosa | 5 min | <10 | 99.9999% |
| | | $4.7 \times 10^6$ | 15 min | <10 | 99.9999% |
| | | | 30 min | <10 | 99.9999% |
| | | | 60 min | <10 | 99.9999% |
| | 6 months | Staphylococcus | 1 min | <10 | 99.9999% |
| | | aureus | 5 min | <10 | 99.9999% |
| | | $5.0 \times 10^6$ | 15 min | <10 | 99.9999% |
| | | | 30 min | <10 | 99.9999% |
| | | | 60 min | <10 | 99.9999% |
| | | Pseudomonas | 1 min | <10 | 99.9999% |
| | | aeruginosa | 5 min | <10 | 99.9999% |
| | | $2.8 \times 10^6$ | 15 min | <10 | 99.9999% |
| | | | 30 min | <10 | 99.9999% |
| | | | 60 min | <10 | 99.9999% |
| | 12 months | Staphylococcus | 1 min | <10 | 99.9999% |
| | | Aureus | 5 min | <10 | 99.9999% |
| | | $5.5 \times 10^6$ | 15 min | <10 | 99.9999% |
| | | | 30 min | <10 | 99.9999% |
| | | | 60 min | <10 | 99.9999% |
| | | Pseudomonas | 1 min | <10 | 99.9999% |
| | | Aeruginosa | 5 min | <10 | 99.9999% |
| | | $4.5 \times 10^6$ | 15 min | <10 | 99.9999% |
| | | | 30 min | <10 | 99.9999% |
| | | | 60 min | <10 | 99.9999% |

TABLE 2d

| | | | | | |
|---|---|---|---|---|---|
| Antibacterial activity (Time Kill Anti-bacterial test) of ECAS 2 over storage | | | | | |
| ECAS SAMPLE | STORAGE TIME | BACTERIA Conc. CFU/ml | EXPOSURE TIME | BACTERIA SURVIVED CFU/ml | PERCENTAGE REDUCTION |
| ECAS 2 | 0 | *Staphylococcus aureus* $8.8 \times 10^6$ | 1 min | <10 | 99.9999% |
| | | | 5 min | <10 | 99.9999% |
| | | | 15 min | <10 | 99.9999% |
| | | | 30 min | <10 | 99.9999% |
| | | | 60 min | <10 | 99.9999% |
| | | *Pseudomonas aeruginosa* $4.7 \times 10^6$ | 1 min | <10 | 99.9999% |
| | | | 5 min | <10 | 99.9999% |
| | | | 15 min | <10 | 99.9999% |
| | | | 30 min | <10 | 99.9999% |
| | | | 60 min | <10 | 99.9999% |
| | 6 months | *Staphylococcus aureus* $7.5 \times 10^6$ | 1 min | <10 | 99.9999% |
| | | | 5 min | <10 | 99.9999% |
| | | | 15 min | <10 | 99.9999% |
| | | | 30 min | <10 | 99.9999% |
| | | | 60 min | <10 | 99.9999% |
| | | *Pseudomonas aeruginosa* $3.8 \times 10^6$ | 1 min | <10 | 99.9999% |
| | | | 5 min | <10 | 99.9999% |
| | | | 15 min | <10 | 99.9999% |
| | | | 30 min | <10 | 99.9999% |
| | | | 60 min | <10 | 99.9999% |
| | 12 months | *Staphylococcus Aureus* $5.0 \times 10^6$ | 1 min | <10 | 99.9999% |
| | | | 5 min | <10 | 99.9999% |
| | | | 15 min | <10 | 99.9999% |
| | | | 30 min | <10 | 99.9999% |
| | | | 60 min | <10 | 99.9999% |
| | | *Pseudomonas Aeruginosa* $4.9 \times 10^6$ | 1 min | <10 | 99.9999% |
| | | | 5 min | <10 | 99.9999% |
| | | | 15 min | <10 | 99.9999% |
| | | | 30 min | <10 | 99.9999% |
| | | | 60 min | <10 | 99.9999% |

All ECAS show good antibacterial activity. The stability results, moreover, show that ECAS 1 and ECAS 2, comprising salts of boric acid and salts of phosphoric acid, respectively, are more stable than ECAS 0 in terms of physicochemical parameters (Tab. 2a) and maintenance of antibacterial activity also after one year, as shown in detail in Tables 2c and 2d.

EXAMPLE 3: In Vitro Antimicrobial Activity of Electrochemically Activated Salt Solutions The in vitro antimicrobial activity of the ECAS 2 against bacteria, yeast and spores was tested. The tests were conducted in triplicate of each, a negative control (buffered sodium chloride-peptone solution), ECAS 2 and a reference product (Floxal®, eyedrops, 0.3% ofloxacin, benzalkoniumchloride, water for injection), against 10 reference strains and 39 clinical isolates.

Each microorganism sample was diluted to a starting concentration of at least $10^5$-$10^6$ CFU/ml. Then, the negative control, the ECAS 2 and the reference product were inoculated with 0.1 ml each and each sample was mixed. At time intervals of 0, 15, and 30 min after inoculation, samples were taken and inactivated to determine the microbial survival.

The reduction in microorganism population was calculated by comparing the initial microbial concentration and the concentration at each incubation interval (both in CFU/mL). The results are shown in Table 3.

| Microorganism | Number | Item | #Tests (N) | 0 | 15 | 30 |
|---|---|---|---|---|---|---|
| *Staphylococcus aureus* | CCM 4223 | Control | 3 | 0 | — | — |
| | | ECAS2 | 3 | 92.9 | >99.4 | >99.4 |
| | | Ref | 3 | 12.0 | >93.6 | >93.6 |
| *Staphylococcus epidermidis* | CCM 2124 | Control | 3 | 0 | — | — |
| | | ECAS2 | 3 | 97.9 | >99.8 | >99.8 |
| | | Ref | 3 | 95.6 | >97.5 | >97.5 |
| *Escherichia coli* | CCM 4517 | Control | 3 | 0 | — | — |
| | | ECAS2 | 3 | 99.7 | >99.9 | >99.9 |
| | | Ref | 3 | >99.4 | >99.4 | >99.4 |
| *Pseudomonas aeruginosa* | CCM 1961 | Control | 3 | 0 | — | — |
| | | ECAS2 | 3 | 95.5 | >99.1 | >99.1 |
| | | Ref | 3 | >90.8 | >90.8 | >90.8 |
| *Acinetobacter calcoaceticus* | CCM 4503 | Control | 3 | 0 | — | — |
| | | ECAS2 | 3 | >99.8 | >99.8 | >99.8 |
| | | Ref | 3 | 54.3 | >98.4 | >98.4 |
| *Enterobacter aerogenes* | CCM 7797 | Control | 3 | 0 | — | — |
| | | ECAS2 | 3 | 86.7 | >99.9 | >99.9 |
| | | Ref | 3 | 60.4 | >98.7 | >98.7 |
| *Streptococcus anginosus* | CCM 7437 | Control | 3 | 0 | — | — |
| | | ECAS2 | 3 | 20.6 | >99.6 | >99.6 |
| | | Ref | 3 | 26.6 | >96.4 | >96.4 |
| *Streptococcus pyogenes* | A1 96/50 | Control | 3 | 0 | — | — |
| | | ECAS2 | 3 | 97.5 | >99.5 | >99.5 |
| | | Ref | 3 | 36.6 | >94.9 | >94.9 |
| *Candida albicans* | CCM 8215 | Control | 3 | 0 | — | — |
| | | ECAS2 | 3 | 98.2 | >99.9 | >99.9 |
| | | Ref | 3 | 1.2 | 28.1 | 30.0 |
| *Aspergillus brasiliensis* | CCM 8222 | Control | 3 | 0 | — | — |
| | | ECAS2 | 3 | 66.5 | >99.7 | >99.7 |
| | | Ref | 3 | 0 | 0 | 0 |

Table 3 (continued): Antimicrobial activity of ECAS 2 in comparison with the reference product Floxal® (referred to as Ref) against clinical isolates displayed in average percent of inhibition.

| Micro-organism | Number | Item | #Tests (N) | Sampling Time in minutes 0 | 15 | 30 |
|---|---|---|---|---|---|---|
| Staphylo-coccus aureus | GAOC 955/1 | Control ECAS2 Ref | 3 3 3 | 0 >98.1 42.3 | — >98.1 >80.8 | — >98.1 >80.8 |
| Staphylo-coccus aureus | GAOC 950/1 | Control ECAS2 Ref | 3 3 3 | 0 83.3 37.7 | — >99.7 >97.1 | — >99.7 >97.1 |
| Staphylo-coccus aureus | DOC 792/1 | Control ECAS2 Ref | 3 3 3 | 0 43.6 4.0 | — >99.6 >95.9 | — >99.6 >95.9 |
| Staphylo-coccus aureus | DOC 838/1 | Control ECAS2 Ref | 3 3 3 | 0 37.2 9.1 | — >99.7 >96.6 | — >99.7 >96.6 |
| Staphylo-coccus aureus | DOC 800/2 | Control ECAS2 Ref | 3 3 3 | 0 46.8 20.7 | — >99.6 >96.3 | — >99.6 >96.3 |
| Staphylo-coccus aureus | DOC 806/1 | Control ECAS2 Ref | 3 3 3 | 0 >99.7 27.3 | — >99.7 >96.7 | — >99.7 >96.7 |
| Staphylo-coccus aureus | DOC 816/1 | Control ECAS2 Ref | 3 3 3 | 0 90.7 70.4 | — >99.8 >98.2 | — >99.8 >98.2 |
| Staphylo-coccus aureus | DOC 818/3 | Control ECAS2 Ref | 3 3 3 | 0 95.9 32.2 | — >99.8 >98.3 | — >99.8 >98.3 |
| Staphylo-coccus aureus | GAOC 997 | Control ECAS2 Ref | 3 3 3 | 0 99.2 81.3 | — >99.8 >98.4 | — >99.8 >98.4 |
| Staphylo-coccus aureus | DOC 833/1 | Control ECAS2 Ref | 3 3 3 | 0 79.1 58.9 | — >99.7 >97.4 | — >99.7 >97.4 |
| Staphylo-coccus aureus | DOC 907 | Control ECAS2 Ref | 3 3 3 | 0 >99.5 42.8 | — >99.5 >94.9 | — >99.5 >94.9 |
| Staphylo-coccus aureus | DOC 885 | Control ECAS2 Ref | 3 3 3 | 0 91.7 44.5 | — >99.8 >97.9 | — >99.8 >97.9 |
| Staphylo-coccus aureus | DOC 890 | Control ECAS2 Ref | 3 3 3 | 0 81.8 44.6 | — >99.5 >94.6 | — >99.5 >94.6 |

Table 3 (continued): Antimicrobial activity of ECAS 2 in comparison with the reference product Floxal® (referred to as Ref) against clinical isolates displayed in average percent of inhibition.

| Micro-organism | Number | Item | #Tests (N) | Sampling Time in minutes 0 | 15 | 30 |
|---|---|---|---|---|---|---|
| Staphylo-coccus aureus | GAOC 979 | Control ECAS2 Ref | 3 3 3 | 0 94.0 41.9 | — >99.9 >98.7 | — >99.9 >98.7 |
| Staphylo-coccus aureus | GAOC 983 | Control ECAS2 Ref | 3 3 3 | 0 81.2 37.9 | — >99.7 >96.7 | — >99.7 >96.7 |
| Staphylo-coccus aureus | DOC 939/1 | Control ECAS2 Ref | 3 3 3 | 0 99.4 87.0 | — >99.8 >97.9 | — >99.8 >97.9 |
| Staphylo-coccus aureus | DOC 955/1 | Control ECAS2 Ref | 3 3 3 | 0 88.2 55.3 | — >99.5 >95.3 | — >99.5 >95.3 |
| Staphylo-coccus aureus | DOC 855/1 | Control ECAS2 Ref | 3 3 3 | 0 26.7 24.2 | — >99.7 83.2 | — >99.7 >97.3 |
| Staphylo-coccus aureus | DOC 862/1 | Control ECAS2 Ref | 3 3 3 | 0 52.8 42.8 | — >99.7 >96.5 | — >99.7 >96.5 |
| Staphylo-coccus aureus | DOC 848/1 | Control ECAS2 Ref | 3 3 3 | 0 94.5 72.2 | — >99.9 >98.6 | — >99.9 >98.6 |

-continued

| Micro-organism | Number | Item | #Tests (N) | Sampling Time in minutes 0 | 15 | 30 |
|---|---|---|---|---|---|---|
| Staphylo-coccus aureus | DOC 849/1 | Control ECAS2 Ret | 3 3 3 | 0 69.6 23.0 | — >99.9 >99.3 | — >99.9 >99.3 |
| Staphylo-coccus aureus | TOOC 227/3 | Control ECAS2 Ret | 3 3 3 | 0 59.2 25.5 | — >99.9 >99.2 | — >99.9 >99.2 |
| Staphylo-coccus aureus | TOOC 226/3 | Control ECAS2 Ref | 3 3 3 | 0 >99.8 51.5 | — >99.9 >97.6 | — >99.9 >97.6 |
| Staphylo-coccus aureus | LVOC 557/1 | Control ECAS2 Ref | 3 3 3 | 0 86.2 52.1 | — >99.8 >97.9 | — >99.8 >97.9 |
| Staphylo-coccus aureus | TOOC 224/1 | Control ECAS2 Ref | 3 3 3 | 0 73.8 60.7 | — >99.8 >97.9 | — >99.8 >97.9 |

Table 3 (continued): Antimicrobial activity of ECAS 2 in comparison with the reference product Floxal® (referred to as Ref) against clinical isolates displayed in average percent of inhibition.

| Micro-organism | Number | Item | #Tests (N) | Sampling Time in minutes 0 | 15 | 30 |
|---|---|---|---|---|---|---|
| Staphylo-coccus aureus | TOOC 243/1 | Control ECAS2 Ref | 3 3 3 | 0 81.6 26.4 | — >99.8 >97.9 | — >99.8 >97.9 |
| Staphylo-coccus aureus | LVOC 550/1 | Control ECAS2 Ref | 3 3 3 | 0 92.5 68.1 | — >99.9 >98.5 | — >99.9 >98.5 |
| Staphylo-coccus aureus | KNOC 467/1 | Control ECAS2 Ref | 3 3 3 | 0 58.2 34.5 | — >99.5 >94.9 | — >99.5 >94.9 |
| Staphylo-coccus aureus | LVOC 559/2 | Control ECAS2 Ref | 3 3 3 | 0 >99.4 68.2 | — >99.4 >93.9 | — >99.4 >93.9 |
| Staphylo-coccus aureus | DOC 854/1 | Control ECAS2 Ref | 3 3 3 | 0 77.8 54.3 | — >99.3 >92.8 | — >99.3 >92.8 |
| Staphylo-coccus aureus | TOOC 236/1 | Control ECAS2 Ref | 3 3 3 | 0 99.5 93.9 | — >99.9 >99.5 | — >99.9 >99.5 |
| Staphylo-coccus aureus | DOC 960/1 | Control ECAS2 Ref | 3 3 3 | 0 98.1 86.9 | — >99.6 >95.9 | — >99.6 >95.9 |
| Staphylo-coccus aureus MR | DOC 873/1 | Control ECAS2 Ref | 3 3 3 | 0 88.4 35.8 | — >99.7 >97.1 | — >99.7 >97.1 |
| Staphylo-coccus aureus MR | DOC 845/1 | Control ECAS2 Ref | 3 3 3 | 0 96.8 14.9 | — >99.6 >95.9 | — >99.6 >95,9 |
| Escher-ichia coli | GAOC 961/1 | Control ECAS2 Ref | 3 3 3 | 0 93.3 73.6 | — >99.8 >97.6 | — >99.8 >98.2 |
| Escher-ichia coli | DOC 958/1 | Control ECAS2 Ref | 3 3 3 | 0 99.5 82.7 | — >99.9 >98.8 | — >99.9 >98.8 |
| Pseudo-monas aeruginosa | DOC 809/1 | Control ECAS2 Ref | 3 3 3 | 0 >99.9 61.4 | — >99.9 >98.7 | — >99.9 >98.7 |
| Serratia marcescens | DOC 920 | Control ECAS2 Ref | 3 3 3 | 0 82.5 81.0 | — >98.7 >87.3 | — >98.7 >87.3 |
| Acineto-bacter pitii | DOC 784/1 | Control ECAS2 Ref | 3 3 3 | 0 67.9 63.4 | — >99.6 >96.3 | — >99.6 >96.3 |

Reference Strains

The reference strains *S. aureus, S. epidermidis, Acinetobacter calcoaceticus, Streptococcus anginosus, Streptococcus pyogenes, Pseudomonas aeruginosa, E. coli, Enterobacter aerogenes, Candida albicans* and *Aspergillus brasiliensis* were susceptible to ECAS 2. The ECAS 2 showed high activity (inhibition of more than 50%) at time 0 against 9/10 microorganisms. An inhibition of more than 90% was determined for 7 microorganisms.

After 15 min the ECAS 2 showed activity (inhibition of more than 99%) against all tested reference strains.

The reference strains *S. aureus, S. epidermidis, Acinetobacter calcoaceticus, Streptococcus anginosus, Streptococcus pyogenes, Pseudomonas aeruginosa, E. coli* and *Enterobacter aerogenes* were susceptible to the reference product Floxal®. The reference product showed high activity (inhibition of more than 50%) at time 0 against 5/10 microorganisms. An inhibition of more than 90% was determined for 3 microorganisms.

After 15 min the reference product showed activity (inhibition of more than 90%) against 8/10 tested reference strains.

Two microorganisms, *Candida albicans* and *Aspergillus brasiliensis*, remained viable (inhibition of less than 50%) during up to 30 min of incubation.

Clinical Isolates

The 39 clinical isolates involved in the study were selected based on the incidence of the strains as collected from conjunctivitis in the medical microbiology laboratory within a one-month period. The most of them (34) were *Staphylococcus aureus* and MRSA, the rest, with lower incidence were *E. coli* (2), *Pseudomonas aeruginosa* (1), *Acinetobacter pitii* (1), and *Serratia marcescenc* (1).

*Staphylococcus aureus* and MRSA

The ECAS 2 showed high activity (inhibition of more than 50%) at time 0 against 30/34 of tested isolates. An inhibition of more than 90% was determined for 16/34 isolates of *S. aureus*/MRSA.

After 15 min the ECAS 2 showed activity (inhibition of more than 99%) against 34/34 isolates.

The reference product showed high activity (inhibition of more than 50%) at time 0 against 14/34 tested *S. aureus*/MRSA isolates. An inhibition of more than 90% was determined for 1/34 isolates.

At 15 min, the reference product showed activity (inhibition of more than 90%) against 32/34 tested isolates.

*E. coli*

The ECAS 2 showed high activity (inhibition of more than 50%) at time 0 against 2/2 of the tested *E. coli* isolates. An inhibition of more than 90% was determined for 2/2 isolates.

The ECAS 2 showed activity (inhibition of more than 99%) against 2/2 tested *E. coli* strains at 15 minutes.

The reference product showed high activity (inhibition of more than 50%) at time 0 against 2/2 of the tested *E. coli* isolates. An inhibition of more than 90% was determined for 0/2 isolates.

The reference product showed activity (inhibition of more than 90%) against 2/2 tested isolates of *E. coli* at 15 minutes.

*Pseudomonas aeruginosa*

The ECAS 2 showed high activity of more than 90% for 1/1 isolate of *Pseudomonas aeruginosa* at 0 min.

At 15 min, the ECAS 2 showed activity (inhibition of more than 99%) against 1/1 tested *Pseudomonas aeruginosa* strain.

The reference product showed high activity (inhibition of more than 50%) against 1/1 and an inhibition of more than 90% against 0 isolates of *Pseudomonas aeruginosa* at time 0.

The reference product showed activity (inhibition of more than 90%) against 1/1 tested isolates of *Pseudomonas aeruginosa* at 15 minutes.

Gram Negative Bacteria (*Serratia, Acinetobacter* Pitii)

The ECAS 2 showed high activity (inhibition of more than 50%) at time 0 against 2/2 isolates of the listed Gram negative bacteria.

At 15 min, the ECAS 2 showed activity (inhibition of more than 99%) against 2/2 isolates.

The reference product showed high activity (inhibition of more than 50%) at time 0 against 2/2 of the listed Gram negative bacteria.

At 15 min, the reference product showed activity (inhibition of more than 90%) against 1/2 tested isolates.

DISCUSSION

The results show that the ECAS 2 possesses strong antimicrobial activity. The spectrum of activity covers gram positive and gram negative bacteria, yeasts and molds. Inhibitory activity was detected against all reference strains (10 strains) and against all of the clinical isolates from conjunctivitis (39 strains) immediately after mixing of test inoculum ($10^5$-$10^6$) with the ECAS 2. With the exception of two cases (*Staphylococcus aureus* GAOC 955/1 and *Serratia marcescens* DOC 920) an inhibition of >99% was determined for all tested strains after 15 min of incubation.

Differences in antimicrobial activity for the reference product Floxal® as compared to the ECAS 2 were particularly observed at time 0. The inhibition determined for the ECAS 2 at time 0 was more effective than the inhibition with the reference product. Further, *Aspergillus brasiliensis* and *Candida albicans* were not susceptible to the reference product at a time interval of up to 30 minutes.

EXAMPLE 4: In Vitro Antiviral Activity of Electrochemically Activated Salt Solutions A. Vero cells were seeded in 24-well plates and treated with dilutions of the ECAS 2 Dil.1:1 and Dil.1:2, either:

I. 24 hours before the infection;

II. 2 hours before the infection;

III. during the infection;

IV. 2 hours post infection; or

V. 6 hours post infection.

The cells were infected with the HSV-1 strains Kupka and ANGpath at a multiplicity of infection (MOI) of 0.01. The cells were collected 24 hours post infection (hpi) and the virus titer was determined by plaque assay. Briefly, the samples were serially diluted and plated onto one-day Vero cell-monolayers in 24- or 6-well tissue plates in duplicates. Afterwards, the cells were overlaid with 1% methylcellulose in normal growth media. 5 days post infection, the cells were fixed and stained with 2% crystal violet in 20% ethanol, and the individual plaques were counted to determine the virus titer in each sample. Samples without treatment (Mock, negative control) and samples treated with ACV (Acyclovir, 100 μmol/l, reference control) were handled in the same manner. The test was performed in two independent experiments, where each of the samples was tested in parallel wells.

B. The HSV-1 strains Kupka and ANGpath, were incubated at a MOI of 0.01 with dilutions of the ECAS 2 either Dil.1:1 or Dil.1:2, in a final volume of 100 μl for either:

I. 12 hours;

II. 8 hours;

III. 6 hours; or

IV. 2 hours.

Then cells, which had been seeded in 24-well plates 24 hours before the infection, were infected with the above mentioned pre-incubated viruses. 24 hpi the cells were collected and the virus titer was determined by a plaque assay, as described above. Samples without treatment (Mock, negative control) and samples treated with Acyclovir (100 μmol/l as reference control) were handled in the same manner. The test was performed in two independent experiments, where each of the samples was tested in parallel wells.

Results

A. A significant reduction in titer of the HSV-1 strain Kupka was detected, when the cells were treated with the ECAS 2 diluted 1:1 at all time points (FIG. 1). Interestingly, the reduction in virus titer in cells treated with the ECAS 2 (1:1) during the infection, or 2 and 6 hpi was even stronger in comparison to the one of ACV treatment at the same time points. The maximal reduction in titer of the HSV-1 strain Kupka, by 6.29 log 10 PFU/ml (p≤0.01), was detected in cells treated with the ECAS 2 diluted 1:1 during infection (Tab. 4).

The ECAS 2 diluted 1:2 did not inhibit virus replication to the extent observed at a dilution 1:1. Nevertheless, when the cells were treated during the infection, a titer reduction by 3.26 log 10 PFU/ml (p≤0.01) was detected compared to mock-treated infected cells.

When the cells were treated with ACV, the maximal reduction in titer of the HSV-1 strain Kupka, by 4.52 log 10 PFU/ml (p≤0.01), was detected in cells treated 2 hpi.

| Dilution | Time of cell treatment with the test product | Reduction in viral titer [log10] |
|---|---|---|
| 1:1 | 24 h before infection | 1.42 |
| | 2 h before infection | 1.74 |
| | during infection | 6.29 |
| | 2 hpi | 4.76 |
| | 6 hpi | 5.67 |
| 1:2 | 24 h before infection | 1.18 |
| | 2 h before infection | 0.40 |
| | during infection | 3.26 |
| | 2 hpi | 0.97 |
| | 6 hpi | 1.55 |
| ACV | 24 h before infection | 1.96 |
| | 2 h before infection | 1.96 |
| | during infection | 3.69 |
| | 2 hpi | 4.52 |
| | 6 hpi | 3.43 |

Similar to the HSV-1 strain Kupka, a significant reduction in titer of HSV-1 ANGpath was detected, when the cells were treated with the ECAS 2 diluted 1:1 at all time points (FIG. 2). Interestingly, the reduction in virus titer in cells treated with the ECAS (1:1) at all time points of treatment was even stronger in comparison to the cell treatment with ACV. The maximal reduction in titer of the HSV-1 strain ANGpath, by 6.11 log 10 PFU/ml (p≤0.01), was detected in cells treated with the ECAS 2 diluted 1:1 during infection (Tab. 5).

The ECAS 2 diluted 1:2 did not inhibit virus replication to the extent observed at a dilution of 1:1. Nevertheless, when the cells were treated at 6 hpi, a reduction in titer by 2.24 log 10 PFU/ml (p≤0.01) compared to mock-treated infected cells was detected.

When the cells were treated with ACV, the maximum reduction in titer of the HSV-1 strain ANGpath, by 2.45, 2.81 and 2.38 log 10 PFU/ml (p≤0.01), was detected in cells treated during infection, at 2 hpi and at 6 hpi, respectively.

| Dilution | Time of cell treatment with the test product | Reduction in viral titer [log10] |
|---|---|---|
| 1:1 | 24 h before infection | 1.98 |
| | 2 h before infection | 2.66 |
| | during infection | 6.11 |
| | 2 hpi | 5.56 |
| | 6 hpi | 4.29 |
| 1:2 | 24 h before infection | 1.46 |
| | 2 h before infection | 0.30 |
| | during infection | 1.91 |
| | 2 hpi | 1.75 |
| | 6 hpi | 2.24 |
| ACV | 24 h before infection | 0.54 |
| | 2 h before infection | 0.61 |
| | during infection | 2.45 |
| | 2 hpi | 2.81 |
| | 6 hpi | 2.38 |

A product is considered as mildly active against a virus in the case the virus titer is reduced at least by 1 log 10 PFU/ml in comparison to the control. A strong antiviral effect of the product is considered when the virus titer is reduced by at least 4 log 10 PFU/ml.

Our results indicate that treatment of cells with the ECAS 2 diluted 1:1 during the infection or at early times post infection could reduce the viral titer at least by 4 log 10 PFU/ml and this potential of the ECAS is not dependent on the HSV-1 strain. Thus, the ECAS 2 according to the invention has the potential to reduce the viral titer, when cells are treated during the infection or at early times post infection.

B. A total reduction in titer of the HSV-1 strain Kupka was detected in infected cells treated with the ECAS 2 diluted 1:1 for all time points. Interestingly, the reduction in virus titer in infected cells treated with the ECAS 2 diluted 1:2 was even stronger in comparison to ACV treatment (FIG. 3). The maximal reduction in titer of the HSV-1 strain Kupka, by 5.74 log 10 PFU/ml (p≤0.01), was detected in infected cells treated with the ECAS 2 diluted 1:1 for all time points and with the ECAS 2 diluted 1:2 for 12 hours (Tab. 6).

| Dilution | Time of virus incubation with the test product | Reduction in viral titer [log10] |
|---|---|---|
| 1:1 | 2 h | 5.74 |
| | 6 h | 5.74 |
| | 8 h | 5.74 |
| | 12 h | 5.74 |
| 1:2 | 2 h | 5.24 |
| | 6 h | 5.24 |
| | 8 h | 5.24 |
| | 12 h | 5.74 |
| ACV | 2 h | 4.62 |
| | 6 h | 3.55 |

-continued

| Dilution | Time of virus incubation with the test product | Reduction in viral titer [log10] |
|---|---|---|
| | 8 h | 5.17 |
| | 12 h | 3.15 |

A total reduction in titer of the HSV-1 strain ANGpath was detected in infected cells treated with the ECAS 2 diluted 1:1 for 2, 8 and 12 h. Interesting, the reduction in virus titer in infected cells treated with the ECAS 2 diluted 1:2 at 6-12 h was even stronger in comparison to ACV treatment (FIG. 4). The maximal reduction in titer of the HSV-1 strain ANGpath, by 7.50 log 10 PFU/ml ($p \leq 0.01$), was detected in infected cells treated with the ECAS 2 diluted 1:1 for 2, 8 and 12 h (Tab. 7).

| Dilution | Time of virus incubation with the test product | Reduction in viral titer [log10] |
|---|---|---|
| 1:1 | 2 h | 7.50 |
| | 6 h | 6.22 |
| | 8 h | 7.50 |
| | 12 h | 7.50 |
| 1:2 | 2 h | 2.38 |
| | 6 h | 3.12 |
| | 8 h | 3.72 |
| | 12 h | 3.69 |
| ACV | 2 h | 2.85 |
| | 6 h | 2.59 |
| | 8 h | 2.97 |
| | 12 h | 2.56 |

The results clearly demonstrate that pre-incubation of virus with the ECAS 2 diluted 1:1 for 2 and more hours significantly reduces the titer of the HSV-1 strain Kupka and ANGpath. Taken together, the ECAS 2 has the potential to directly influence the virus and mediate the inhibition of HSV-1 replication, when the virus is pre-incubated with the test product for 2 hours and more before the infection.

The ECAS 2 has the potential to reduce the viral titer, when cells are treated with the ECAS 2 during the infection or at early times post infection. Moreover, the ECAS 2 has the potential to reduce the viral titer, when virus is treated with the ECAS 2 for two hours and more before the infection.

The results presented here clearly demonstrate that the ECAS 2 has basically the same antiviral effect as ACV, because the ECAS 2 can inhibit the virus replication, expressed as a reduction of viral titer, when cells are treated with the ECAS 2 during the infection or at early times post HSV-1 infection, and inhibit the virus replication, expressed as a reduction of viral titer, when virus is treated with the ECAS 2 for 2 hours and more before HSV-1 infection.

EXAMPLE 5: In Vivo Antimicrobial Activity of Electrochemically Activated Salt Solutions In Vivo Activity Against *Staphylococcus aureus*

The antimicrobial effect of ECAS 2 in vivo was examined in eye balls of young New Zealand albino female rabbits. The conjunctiva of the rabbit right eye was injured under the condition of Isoflurane anesthesia. *Staphylococcus aureus* DOC 845/1 for inoculation was prepared from an overnight suspension after centrifugation, washing in saline and appropriate dilution to a suspension of $10^6$ CFU and was instilled (injection in a volume of 50 µl) to mimic a branch injury. *S. aureus* was allowed to incubate for 48 hours.

After 48 h, the infected rabbits' eyeballs were examined. All animals (24 New Zealand albino female rabbits) showed no findings before the first treatment when examined according to Draize's eye test (cornea and iris, included) except of conjunctivitis as confirmed by ophthalmologists. Based on the grading of conjunctivitis (W. Behrens-Baumann and T. Begall, 1997) after 48 h the animals were distributed into three groups (group I, II and III) in a way to obtain comparable conjunctive inflammatory scoring in each group.

The treatment of infected eyes started 48 hours after infection. Animals in group I were treated with normal sterile physiological saline (negative control/untreated group); animals in group II were treated with the ECAS 2 animals in group III were treated with commercial eye drops Floxal® containing ofloxacin (0.3% w/v in in water for injection, preservative-free; positive control). All three groups received 30 µL treatment solution per eyeball, respectively. The solution was sterilely instilled into the right conjunctival sac with a micropipette according to the schedule (every 3 hours for 6 days), spread on the entire eyeball and held for a few seconds. The left eye served as a control. The treatment for the different groups is summarized in Table 8.

TABLE 8

| In vivo experiment design | | | |
|---|---|---|---|
| Group designation | Concentration/description | Dose (µl) | Number of Animals |
| group I (infected/without treatment) | Physiological saline 0.9% | 30 | 8 |
| group II (infected/with therapeutic treatment-ECAS 2 | as delivered | 30 | 8 |
| group III (infected/with therapeutic treatment-Floxal ®) | ofloxacin 0.3% | 30 | 8 |

Ophthalmological Examination

Ophthalmological examinations were performed daily just before the first treatment, except for the fourth day of treatment. The main parameter—conjunctival hyperaemia—was graded 1, 2, 3 or 4 for each quadrant according to Draize eye test (Table 9) (J. Draize et al., 1944). The scoring was performed by two persons; the left eye was used as a control. Ophthalmological examination before the first treatment and at the final ophthalmological examination included also the cornea and the iris.

TABLE 9

Scale of weighted scores for grading the severity of conjunctiva lesions

| Lesion | Score |
|---|---|
| A. Redness (refers to palpebral conjunctiva only) | |
| Vessels definitely injected above normal | 1 |
| More diffuse, deeper crimson red, individual vessels not easily discernible | 2 |
| Diffuse beefy red | 3 |
| B. Chemosis | |
| Any swelling above normal (includes nictitating membrane) | 1 |
| Obvious swelling with partial eversion of the lids | 2 |
| Swelling with lids about half closed | 3 |
| Swelling with lids about half closed to completely closed | 4 |
| C. Discharge | |
| Any amount different from normal (does not include small amount observed in inner canthus of normal rabbits) | |
| Discharge with moistening of the lids and hairs just adjacent to the lids | 2 |
| Discharge with moistening of the lids and considerable area around the eye | 3 |

Microbiological Evaluation

Swabs were taken from the infected eye 48 hours after inoculation and every two days. The swabs were transported in sterile transport media before dilution and cultured using spread plate method. Residual antimicrobial agent in the recovery agar could artificially depress the recovery of viable cells. For this reason, the residual antibacterial activity was inactivated by dilution as described below.

Aliquots of 0.1 mL were serially diluted 10× in sterile buffered saline. The samples from rabbits treated with Floxal® were inactivated in buffered sodium chloride peptone solution, pH 7.0+5% Tween+0.3% Lecithin+0.1% Histidine. Samples from each dilution were plated in triplicate by pipetting 100 μL on the Tryptone Soy agar and spreading, and incubated at 37° C. for 48 h. The number of CFUs was counted.

Results

The colony-forming units observed on each of the three plates/dilution per animal were counted. The obtained individual CFU values were transformed logarithmically prior to statistical assessment. Student's t-test was applied to compare the LogCFUs observed in the three treatment groups. A significance level of $P<0.05$ was adopted. Mann Whitney (Wilcoxon's) test was adopted to compare the clinical score for conjunctiva in component groups. The statistical analysis was performed using Statgraphics™ Centurion software.

Ophthalmological Evaluation

Twenty-four hours after inoculation the first ophthalmological examination was performed to check the onset of the infection process. The results are shown in Table 10.

The examination just before the start of the treatment (48 h) confirmed the development of conjunctivitis in all animals. It was also confirmed that there were no pathological findings in the cornea and iris in any of the animals involved in the study (Table 11).

The infected eyes were controlled six times. Results of the ophthalmological examinations expressed as summary score are presented in Table 10. After the last evaluation (144 h) photographic documentation was done.

Summary score and average score for all time points are documented in FIG. 5 and FIG. 6.

TABLE 10

Ophthalmological evaluation-Individual score

| Group | No. in the Group | No. | 24 h | 48 h | 72 h | 96 h | 144 h | 168 h |
|---|---|---|---|---|---|---|---|---|
| Control | 1 | 1 | 1 | 16 | 8 | 6 | 5 | 2 |
| (I) | 2 | 2 | 1 | 9 | 12 | 14 | 6 | 2 |
| | 3 | 3 | 14 | 12 | 6 | 4 | 0 | 0 |
| | 4 | 4 | 8 | 6 | 2 | 8 | 0 | 0 |
| | 5 | 5 | 6 | 5 | 2 | 10 | 3 | 0 |
| | 6 | 6 | 8 | 16 | 14 | 12 | 6 | 1 |
| | 7 | 7 | 4 | 8 | 14 | 11 | 2 | 0 |
| | 8 | 8 | 1 | 8 | 4 | 8 | 1 | 0 |
| | Mean ± SD | | 5.38 ± 4.60 | 10.0 ± 4.24 | 7.75 ± 5.06 | 9.13 ± 3.27 | 2.88 ± 2.53 | 0.63 ± 0.92 |
| | Summary Score | | 43 | 80 | 62 | 73 | 23 | 5 |
| ECAS 2 | 1 | 9 | 1 | 16 | 6 | 10 | 0 | 0 |
| (II) | 2 | 10 | 11 | 10 | 14 | 8 | 2 | 1 |
| | 3 | 11 | 5 | 10 | 6 | 5 | 1 | 0 |
| | 4 | 12 | 7 | 12 | 8 | 14 | 3 | 0 |
| | 5 | 13 | 4 | 4 | 2 | 3 | 0 | 0 |
| | 6 | 14 | 7 | 8 | 10 | 7 | 4 | 0 |
| | 7 | 15 | 6 | 6 | 8 | 5 | 3 | 1 |
| | 8 | 16 | 6 | 8 | 8 | 7 | 1 | 0 |
| | Mean ± SD | | 5.88 ± 2.85 | 9.25 ± 3.69 | 7.75 ± 3.45 | 7.38 ± 3.42 | 1.75 ± 1.49 | 0.25 ± 0.46 |
| | Summary Score | | 47 | 74 | 62 | 59 | 14 | 2 |
| | 1 | 17 | 13 | 16 | 11 | 12 | 1 | 0 |
| | 2 | 18 | 6 | 11 | 11 | 9 | 1 | 0 |

TABLE 10-continued

Ophthalmological evaluation-Individual score

| Group | No.in the Group | No. | 24 h | 48 h | 72 h | 96 h | 144 h | 168 h |
|---|---|---|---|---|---|---|---|---|
| | 3 | 19 | 2 | 10 | 14 | 10 | 2 | 0 |
| | 4 | 20 | 8 | 7 | 7 | 5 | 1 | 0 |
| | 5 | 21 | 11 | 8 | 7 | 6 | 0 | 0 |
| | 6 | 22 | 5 | 10 | 8 | 6 | 2 | 1 |
| | 7 | 23 | 3 | 6 | 5 | 3 | 0 | 0 |
| | 8 | 24 | 1 | 6 | 3 | 5 | 0 | 0 |
| | Mean ± SD | | 6.13 ± 4.29 | 9.25 ± 3.33 | 8.25 ± 3.58 | 7.00 ± 3.02 | 0.88 ± 0.83 | 0.13 ± 0.35 |
| | Summary Score | | 49 | 74 | 66 | 56 | 7 | 1 |

TABLE 11

Ophthalmologists' control

| Group | No.in the Group | No. | 48 h | | | 192 h | | |
|---|---|---|---|---|---|---|---|---|
| | | | conjunctiva | iris | cornea | conjunctiva | iris | cornea |
| Control | 1 | 1 | +++ | − | − | + | − | − |
| (I) | 2 | 2 | ++ | − | − | − | − | − |
| | 3 | 3 | +++ | − | − | − | − | − |
| | 4 | 4 | ++ | − | − | − | − | − |
| | 5 | 5 | ++ | − | − | +* | − | − |
| | 6 | 6 | +++(+) | − | − | − | − | − |
| | 7 | 7 | +++ | − | − | − | − | − |
| | 8 | 8 | +++ | − | − | − | − | − |
| ECAS 2 | 1 | 9 | ++ | − | − | − | − | − |
| (II) | 2 | 10 | +++ | − | − | − | − | − |
| | 3 | 11 | +++ | − | − | +* | − | − |
| | 4 | 12 | +++ | − | − | − | − | − |
| | 5 | 13 | ++ | − | − | − | − | − |
| | 6 | 14 | ++− +++ | − | − | − | − | − |
| | 7 | 15 | ++−+++ | − | − | − | − | − |
| | 8 | 16 | ++ | − | − | − | − | − |
| Floxal ® | 1 | 17 | ++−+++ | − | − | − | − | − |
| (III) | 2 | 18 | +++ | − | − | − | − | − |
| | 3 | 19 | +++(+) | − | − | − | − | − |
| | 4 | 20 | +++ | − | − | − | − | − |
| | 5 | 21 | +++ | − | − | − | − | − |
| | 6 | 22 | +++ | − | − | − | − | − |
| | 7 | 23 | +++(+) | − | − | − | − | − |
| | 8 | 24 | + | − | − | − | − | − |

*this rabbit had already a score of "0" when evaluated by the (168 h). The evaluation of the local finding was performed independently by a team of two veterinarians (24, 48, 72, 96, 144, 168 h) and complete evaluation by an ophthalmologist (192 h). The discrepancy is probably the result of differences in the criteria set by these evaluators.

Both ECAS 2 and Floxal® treatment showed a reduction in the symptoms during the time after infection compared with the control which showed increased symptoms after 96 h. Based on the clinical score results (Table 10) it is inferred that after the first day of the treatment (72 h) there was a slight reduction in the symptoms of hyperaemia, chemosis and discharge in all three groups.

After two days of treatment (96 h) a progress of chemosis was not observed in ECAS 2 (II) and Floxal® (III) groups in contrast to the control group (Table 12). In both treatment groups (II and III) the chemosis was in a reduced range.

After four days of treatment the ECAS2 group showed effective clinical cure in 4/8 animals (score 0-1) whilst the Floxal® treated group showed effective clinical cure in 6/8 animals. Eight days post infection (6 dosing days) complete clinical cure was observed in 6/8 animals of the ECAS 2 group whereas in the Floxal® treated group absence of clinical slight symptoms of conjunctivitis was observed in 7/8 animals. The process of infection eradication was relatively fast not allowing to perform a comparison at more time points.

TABLE 12

Score for hyperemiae, chemosis and discharge score in the eradication phase of infection

| Group | 72 h | | | 96 h | | | 144 h | | |
|---|---|---|---|---|---|---|---|---|---|
| | H | CH | D | H | CH | D | H | CH | D |
| Control | 39 | 23 | 0 | 35 | 38 | 0 | 16 | 5 | 2 |
| ECAS 2 | 38 | 24 | 0 | 32 | 27 | 0 | 9 | 5 | 0 |
| Floxal ® | 37 | 29 | 0 | 30 | 26 | 0 | 7 | 0 | 0 |

H-hyperaemia,
CH-chemosis,
D-discharge

Microbiological Examination

After two days of treatment (96 h) the treatment with the ECAS 2 reduced the number of *S. aureus* by approximately 1.2 log CFU compared to that at the start of the treatment (FIG. 7). The reduction was not statistically significant compared to that of the untreated control at P=0.05

(P=0.2679) primarily due to the high variability of the data. The swabs were negative in 2/8 rabbits (Table 13).

After two days of the treatment (96 h), Floxal® produced approximately 1.6 log reduction in CFU relative to the counts determined at the start of the treatment (FIG. 7). The reduction was not statistically significant compared to that of the untreated control at P=0.05 (P=0.0768). The variability of outcoming data was substantial in this case too. The swabs were negative in 3/8 rabbits.

TABLE 13

| Microbiological examination of ocular swabs | | | | | | | |
|---|---|---|---|---|---|---|---|
| | | 48 h | | 96 h | | 144 h | |
| Group | No. | CFU | log CFU | CFU | log CFU | CFU | log CFU |
| Control (I) | 1 | 8958 | 3.95 | 1517 | 3.18 | 585 | 2.77 |
| | 2 | 19250 | 4.28 | 2440 | 3.38 | 1 | 0 |
| | 3 | 10458 | 4.02 | 221 | 2.34 | 1 | 0 |
| | 4 | 7271 | 3.86 | 244 | 2.38 | 1 | 0 |
| | 5 | 9333 | 3.97 | 16667 | 4.22 | 1 | 0 |
| | 6 | 515 | 2.71 | 1065 | 3.03 | 1 | 0 |
| | 7 | 7650 | 3.88 | 9967 | 3.99 | 1 | 0 |
| | 8 | 2850 | 3.45 | 1018 | 3.01 | 1 | 0 |
| Mean ± SD | | | 3.77 ± 0.48 | | 3.20 ± 0.67 | | 0.35 ± 0.98 |
| ECAS 2 (II) | 9 | 44250 | 4.65 | 15333 | 4.18 | 1 | 0 |
| | 10 | 5909 | 3.77 | 15983 | 4.20 | 1 | 0 |
| | 11 | 3342 | 3.52 | 1 | 0 | 1 | 0 |
| | 12 | 48167 | 4.68 | 55 | 1.74 | 1 | 0 |
| | 13 | 658 | 2.82 | 6800 | 3.83 | 1 | 0 |
| | 14 | 1428 | 3.15 | 5017 | 3.70 | 1 | 0 |
| | 15 | 3925 | 3.59 | 42 | 1.62 | 1 | 0 |
| | 16 | 676 | 2.83 | 1 | 0 | 1 | 0 |
| Mean ± SD | | | 3.62 ± 0.73 | | 2.41 ± 2.72 | | 0.0 |
| Floxal (III) | 17 | 15025 | 4.18 | 4750 | 3.67 | 1 | 0 |
| | 18 | 5683 | 3.75 | 43 | 1.63 | 1 | 0 |
| | 19 | 6517 | 3.81 | 1933 | 3.28 | 1 | 0 |
| | 20 | 4217 | 3.63 | 750 | 2.87 | 1 | 0 |
| | 21 | 5050 | 3.70 | 1 | 0 | 1 | 0 |
| | 22 | 10433 | 4.02 | 9583 | 3.98 | 1 | 0 |
| | 23 | 58 | 1.76 | 1 | 0 | 1 | 0 |
| | 24 | 6608 | 3.82 | 1 | 0 | 1 | 0 |
| Mean ± SD | | | 3.58 ± 0.76 | | 1.93 ± 1.74 | | 0.0 |

Conclusion

In this investigation, the focus lies on analyzing the activity of the ECAS 2 in comparison with that of Floxal® by using rabbits with *Staphylococcus aureus* induced conjunctivitis. The efficacy study was done in the right eye balls of young New Zealand albino female rabbits infected with log phase culture of the clinical isolate *S. aureus* DOC 845/1. The anti-conjunctivitis efficacy was evaluated by monitoring the symptoms and scoring of each group. At days 1, 2, 3, 4, 6 and 7 ophthalmological evaluations were done, and the swabs tests for mean bacterial counts were taken every $2^{nd}$ day.

In the group treated with the ECAS there was a considerable treatment effect which distinguished from day 5 (96 h) on. Both in the ECAS 2 and Floxal® treated groups the conjunctival score clinically decreased when compared to the control group.

The clinical score results registered on day 7 (144 h) revealed clear differences between the treated and untreated groups accomplishing germ elimination.

Further, no evidence of local intolerance in the ECAS 2 group was observed.

In Vivo Activity Against *Pseudomonas aeruginosa*

*Pseudomonas aeruginosa* is one of the most commonly isolated pathogens from contact lens-associated ulcerative incidents. Patients infected with *P. aeruginosa* develop severe ulcers and often require more extensive treatments than patients with infections caused by other pathogens. Corneal destruction during *P. aeruginosa* infection is rapid, and perforation and/or loss of vision is possible within 24 h.

The intrastromal injection of bacteria is not analogous, in terms of the route of inoculation, to the most common forms of human keratitis. The invasion of tissue by bacteria from the corneal surface is the more natural means of initiating infection. However, topical inoculations often fail to produce an infection or yield infections in an imprecise fashion (large variations in number of bacteria in the tissue) (O'Callaghan et al., 1999).

Because the rabbit cornea has been a standard model for numerous ocular studies, data can be extrapolated to the therapy of human keratitis (O'Brien et al., 2003). Studies of experimental bacterial keratitis have demonstrated that the tissue damage is mediated by a combination of bacterial host factors.

The aim of the study was to evaluate the effects of the ECAS in experimental keratitis. Intrastromal *Pseudomonas aeruginosa* was given to the right eye of 15 rabbits. The rabbits were divided equally into three treatment groups (n=5): saline (control group I), ECAS 2 (test product group II) and Floxal® (reference group III).

The treatment of *Pseudomonas*-infected corneas started 6 hours after infection based on clinical signs. Treatment products were administered every 60 min with 19 doses in total. The same treatment schedule was applied in group IV for evaluation of non-infected rabbits with the ECAS treatment.

Group I (infected without treatment—I): treated with physiological saline

Group II (infected with treatment—II): animals received treatments with the ECAS 2. 40 µl of ECAS 2 was sterilely instilled into the right conjunctival sac with a micropipette according to the schedule. The eye lids were gently closed for 10-15 seconds. The left eye served as the control.

Group III (infected with treatment—III): animals received treatments with Floxal® in a volume of 40 µl sterilely instilled into the right conjunctival sac with a micropipette according to the schedule. The eye lids were gently closed for 10-15 seconds. The left eye served as the control.

Group IV (not infected with treatment—IV): animals received treatments with 40 µl of ECAS 2 sterilely instilled into the right conjunctival sac with a micropipette according to the schedule. The eye lids were gently closed for 10-15 seconds. The left eye served as the control.

Directly before the first treatment, 6, 17 and 19 h after inoculation, the eyes were examined with a slit lamp to assess the infection development. One hour after the last application the rabbits were sacrificed by an overdosing of Thiopental and cornea were collected for bacterial count.

Microbiological Evaluation

The corneas were aseptically removed, dissected, transferred to tubes, weighed and cut into multiple pieces. The tissues were homogenized in an ice bath by a tissue homogenizer at 20 000 rpm twice for 30 sec in 0.5 mL of sterile phosphate-buffered saline and aliquots were serially diluted 10× in sterile buffered sodium chloride peptone solution. The animals treated with the reference product were serially diluted in buffered sodium chloride peptone solution+5% Tween+0.3% Lecithin+0.1% Histidine for inactivation of residual reference product. Samples from each dilution were plated in triplicate by pipetting 100 µL on Tryptone Soy agar (TSA) and Cetrimid agar and spreading, and incubated at 37° C. for 48 h. The viable CFUs were counted. The number of viable *Pseudomonas aeruginosa* was expressed per 100 mg of cornea (Table 14 and FIG. 8).

To confirm that the infection process was located in the eye structures only and to exclude secondary contamination, swabs were collected from the conjunctive sack 10 hours after infection from all animals.

TABLE 14

| | Results of microbiological examination of cornea 1 hour after the last treatment | | | | | | |
|---|---|---|---|---|---|---|---|
| | | | | | CFU per cornea | | |
| | Cornea | CFU per plate | | | CFU/1 mL cornea | CFU/100 mg cornea | Log CFU/100 mg cornea |
| No. | (mg) | TSA | TSA | Cetrimid Dilution | homogenate | homogenate | homogenate |
| 1/1 | 0.0253 | 0 | 0 | 0 | 1 | <10 | <40 | <1.6 |
| 1/2 | 0.025 | 77 | 112 | 85 | $10^2$ | $91 \times 10^3$ | $364 \times 10^3$ | 5.56 |
| 1/3 | 0.0313 | 55 | 48 | 43 | $10^2$ | $49 \times 10^3$ | $157 \times 10^3$ | 5.19 |
| 1/4 | 0.0358 | 23 | 16 | 10 | $10^4$ | $16 \times 10^5$ | $45 \times 10^5$ | 6.65 |
| 1/5 | 0.0282 | 58 | 48 | 39 | $10^4$ | $48 \times 10^5$ | $170 \times 10^5$ | 7.23 |
| 2/1 | 0.0402 | 150 | 150 | 168 | $10^2$ | $156 \times 10^3$ | $388 \times 10^3$ | 5.59 |
| 2/2 | 0.037 | 74 | 45 | 38 | $10^2$ | $52 \times 10^3$ | $141 \times 10^3$ | 5.15 |
| 2/3 | 0.0477 | 24 | 15 | 13 | $10^2$ | $17 \times 10^3$ | $36 \times 10^3$ | 4.56 |
| 2/4 | 0.0386 | 0 | 0 | 0 | 1 | <10 | <26 | <1.41 |
| 2/5 | 0.0591 | 0 | 0 | 0 | 1 | <10 | <17 | <1.23 |
| 3/1 | 0.0346 | 0 | 0 | 0 | 1 | <10 | <29 | <1.46 |
| 3/2 | 0.0406 | 0 | 0 | 0 | 1 | <10 | <25 | <1.39 |
| 3/3 | 0.0297 | 0 | 0 | 0 | 1 | <10 | <34 | <1.53 |
| 3/4 | 0.0266 | 0 | 0 | 0 | 1 | <10 | <38 | <1.58 |
| 3/5 | 0.037 | 0 | 0 | 0 | 1 | <10 | <27 | <1.43 |
| 4/1 | 0.0515 | 0 | 0 | 0 | 1 | <10 | <19 | <1.28 |
| 4/2 | 0.0338 | 0 | 0 | 0 | 1 | <10 | <30 | <1.48 |
| 4/3 | 0.0356 | 0 | 0 | 0 | 1 | <10 | <28 | <1.45 |
| 4/4 | 0.0331 | 0 | 0 | 0 | 1 | <10 | <30 | <1.48 |
| 4/5 | 0.0387 | 0 | 0 | 0 | 1 | <10 | <26 | <1.41 |

The treatment of rabbit eyes infected with *Pseudomonas aeruginosa* from 6 to 19 h post infection with the ECAS 2 reduced the number of *Pseudomonas aeruginosa* organisms by approximately 1.6 log CFU/100 mg cornea compared to that of the untreated control group (from $4.4 \times 10^6$ to $1.1 \times 10^5$ CFU/100 mg cornea) (FIG. 8). The % residual number of bacteria after treatment with ECAS2 was 2.6% of the control group.

Floxal® reduced the number of bacteria from $4.4 \times 10^6$ to 30.6 CFU/100 mg of cornea, i.e. to a residual % number of bacteria equivalent to <0.1% relative to the saline control. Although the bacteria % reduction generated by Floxal® was slightly higher than by the ECAS 2, the difference between the Floxal® treated group and the ECAS 2 treated group was not statistically significant at P=0.05.

This result strongly proves the great therapeutic potential of the ECAS2 in the treatment of bacterial keratitis.

The present invention covers the following items:
1. Electrochemically activated salt solution (ECAS) comprising
    a content of total chlorine of between 1 and 500 mg/l, preferably 100-450 mg/l,
    a content of chloride of between 2 and 8 g/l, preferably 3-7 g/l,
    a redox potential of +150 to +1,350 mV, preferably +600 to +1,100 mV, more preferably +700 to +1,050 mV, more preferably +700 to +1,000 mV,
    an osmolality of 20-800, preferably 200-400 mOsm/kg, more preferably 250-350 mOsm/kg,
    a pH value of 6.0-7.8, preferably 7.1-7.4, and optionally at least one (salt of) boric acid and/or at least one (salt of) phosphoric acid.

2. Electrochemically activated salt solution (ECAS) according to item 1, which is stable over one year, preferably over two years, when stored in a closed, high-density polyethylene (HDPE) container at 20° C.

3. Electrochemically activated salt solution (ECAS) according to item 1 or 2 comprising at least one (salt of) phosphoric acid, preferably in an amount of 0.01-1000 g/l, more preferably 0.1-100 g/l.

4. Electrochemically activated salt solution (ECAS) according to any of the preceding items, comprising at least one (salt of) boric acid, preferably in an amount of 0.01 to 1000 g/l, more preferably 0.1-500 g/l.

5. Electrochemically activated salt solution (ECAS) according to any of the preceding items, which contains hypochlorite ions and/or hypochlorous acid, particularly in a total concentration of 1 to 10000 mg/l, more preferably in a total concentration of 10 to 1000 mg/l.

6. Electrochemically activated salt solution (ECAS) according to any of the preceding items, wherein the total content of chlorite and chlorate ions is less than 10 mg/l.

7. Electrochemically activated salt solution (ECAS) according to any of the preceding items, wherein the total content of heavy metals and heavy metal ions is less than 10 μg/g, preferably less than 6 μg/g, and preferably the content of each individual heavy metal and heavy metal ion is preferably less than 0.5 μg/g.

8. Electrochemically activated salt solution (ECAS) according to any of the preceding items, further comprising at least one viscosity-increasing agent, such as a polymer.

9. Electrochemically activated salt solution (ECAS) according to item 8, wherein the polymer is selected from the group consisting of cellulose, cellulose derivatives, polysaccharides, such as glucosaminoglycans, polyvinyl alcohol, polyvinyl pyrrolidone, silica gel, and metasilicates of magnesium and/or aluminum.

10. Electrochemically activated salt solution (ECAS) according to any of the preceding items, which does not contain an additional therapeutically active agent, such as a drug.

11. Electrochemically activated salt solution (ECAS) according to any of the preceding items, which does not contain an additional preservative.

12. Pharmaceutical preparation comprising an electrochemically activated salt solution (ECAS) according to any of items 1-11.

13. Pharmaceutical preparation according to item 12 further comprising at least one pharmaceutically acceptable excipient.

14. Electrochemically activated salt solution (ECAS) according to any of items 1-11 for use in treating infections, e.g. caused by bacteria, fungi and/or viruses.

15. Electrochemically activated salt solution (ECAS) for use according to item 14, wherein the bacteria and/or fungi are selected from the group consisting of *Staphylococcus aureus*, methicillin-resistant *Staphylococcus aureus*, *Escherichia coli*, *Staphylococcus epidermidis*, *Pseudomonas aeruginosa*, *Acinetobacter calcoaceticus*, *Enterobacter aerogenes*, *Streptococcus anginosus*, *Streptococcus pyogenes*, *Candida albicans*, *Aspergillus brasiliensis*, *Serratia marcescens* and *Acinetobacter pitii*.

16. Electrochemically activated salt solution (ECAS) for use according to item 14, wherein the viruses are selected from the group consisting of adenoviruses, enteroviruses and herpesviruses, such as Herpes simplex virus 1 and 2.

17. Electrochemically activated salt solution (ECAS) for use according to item 14-16 in treating eye infections.

18. Electrochemically activated salt solution (ECAS) for use according to any of items 14-17 in treating conjunctivitis, keratitis, blepharitis, and/or endophthalmitis.

19. Electrochemically activated salt solution (ECAS) for use according to any of items 14-18 in treating conjunctivitis, particularly bacterial conjunctivitis.

20. Electrochemically activated salt solution (ECAS) for use according to any of items 14-19, which is administered topically onto the eye, the lacrimal sac and/or the lid.

21. Electrochemically activated salt solution (ECAS) for use according to any of items 14-20, which is administered onto the eye directly after infection.

22. Process for producing an electrochemically activated salt solution (ECAS) according to any of items 1-11 comprising the steps:
(i) electrolyzing an aqueous chloride solution in an electrolysis reactor,
(ii) optionally adding at least one (salt of) boric acid and/or at least one (salt of) phosphoric acid, and
(iii) optionally diluting the ECAS by adding water for injection.

23. Process according to item 22, wherein the electrolysis reactor includes a cylindrical cathode, which is mounted coaxially within a cylindrical anode.

24. Process according to item 22 or 23, wherein the chloride solution has a concentration of up to 10 g/l.

25. Process according to any of items 22-24, wherein the electrolysis is conducted at a current of 10.0-30.0 A, preferably 15.0-20.0 A.

26. Process according to any of items 22-25, wherein the electrolysis reactor is configured for continuous electrolysis.

The invention claimed is:

1. A closed high-density polyethylene (HDPE) container comprising:
an electrochemically activated salt solution (ECAS) stored in the closed HDPE container, wherein the ECAS comprises:
a content of total chlorine of between 100 and 450 mg/l,
a content of chloride of between 3 and 7 g/l,
a redox potential of +700 to +1,050 mV,
an osmolality of 250-350 mOsm/kg,
a pH value of 7.1-7.8, and
at least one of boric acid, a salt of boric acid, phosphoric acid, and a salt of phosphoric acid,
wherein, if present, the boric acid or the salt of boric acid is in an amount of 0.1-500 g/l,
wherein, if present, the phosphoric acid or the salt of phosphoric acid is in an amount of 0.1-100 g/l, and
wherein the redox potential of the ECAS stored in the closed HDPE container is reduced by 10% or less after storage for one year at 20° C.

2. The HDPE container of claim 1, wherein the ECAS comprises the phosphoric acid or the salt thereof.

3. The HDPE container of claim 1, wherein the ECAS comprises the boric acid or the salt thereof.

4. The HDPE container of claim 1, wherein the ECAS further comprises hypochlorite ions and/or hypochlorous acid.

5. The HDPE container of claim 1, wherein the ECAS further comprises at least one viscosity-increasing agent.

6. The HDPE container of claim 1, wherein the ECAS does not comprise an additional therapeutically active agent.

7. The HDPE container of claim 1, wherein the ECAS does not comprise an additional preservative.

8. A process for producing the ECAS stored in the HDPE container of claim 1, the process comprising:
(i) electrolyzing an aqueous chloride solution in an electrolysis reactor,
(ii) optionally adding the at least one of boric acid, the salt of boric, phosphoric acid, and the salt of phosphoric acid,
(iii) optionally diluting the ECAS by adding water for injection, and
(iv) storing the ECAS in the HDPE container.

9. The process of claim 8, wherein the electrolysis is conducted at a current of 10.0-30.0 A.

10. The HDPE container of claim 1, wherein said redox potential of the ECAS is +700 to +1,000 mV.

11. The HDPE container of claim 4, wherein said hypochlorite ions and/or hypochlorous acid of the ECAS are in a total concentration of 10 to 1000 mg/l.

12. The HDPE container of claim 1, wherein the redox potential of said ECAS is reduced by 30% or less after 24 months of storage.

* * * * *